(12) United States Patent
Andjelkovic et al.

(10) Patent No.: US 8,344,027 B2
(45) Date of Patent: Jan. 1, 2013

(54) 4-DIMETHYLAMINOBUTYRIC ACID DERIVATIVES

(75) Inventors: Mirjana Andjelkovic, Basel (CH); Simona M. Ceccarelli, Basel (CH); Odile Chomienne, Altkirch (FR); Gerald Lewis Kaplan, New York, NY (US); Patrizio Mattei, Riehen (CH); Jefferson Wright Tilley, North Caldwell, NJ (US)

(73) Assignee: Hoffmann-La Roche Inc., Nutley, NJ (US)

( * ) Notice: Subject to any disclaimer, the term of this patent is extended or adjusted under 35 U.S.C. 154(b) by 549 days.

(21) Appl. No.: 12/430,934

(22) Filed: Apr. 28, 2009

(65) Prior Publication Data

US 2009/0270505 A1  Oct. 29, 2009

(30) Foreign Application Priority Data

Apr. 29, 2008 (EP) .................................. 08155323

(51) Int. Cl.
*A61K 31/195* (2006.01)
*C07C 229/00* (2006.01)
(52) U.S. Cl. .................... 514/563; 562/561; 562/564
(58) Field of Classification Search .................. None
See application file for complete search history.

(56) References Cited

U.S. PATENT DOCUMENTS

| 4,632,925 | A | 12/1986 | Mullin, Jr. et al. |
| 6,444,701 | B1 | 9/2002 | Giannessi et al. |
| 2010/0105900 | A1* | 4/2010 | Pauls et al. .................... 544/168 |

FOREIGN PATENT DOCUMENTS

| EP | 127098 | 12/1984 |
| WO | WO 99/59957 | 11/1999 |
| WO | WO 2006/092204 | 9/2006 |
| WO | WO 2008/015081 | 2/2008 |
| WO | WO 2008/109991 | 9/2008 |
| WO | 2009/132978 | 11/2009 |

OTHER PUBLICATIONS

Silverman (The Organic Chemistry of Drug Design and Drug Action, 1992, pp. 15-20).*
Jackson et al., Biochem. J., 341, pp. 483-489 (1999).
Jackson et al., J. Biol. Chem., 275, pp. 19560-19566 (2000).
Evans et al., Tetrahedron, 59, pp. 7973-7981 (2003).
Lin et al., J. Org. Chem., 72, pp. 9471-9480 (2007).
Giannessi, F. et al, Database CA Online Chemical Abstracts Service, XP002539907, database accession No. 2002:954524 & J. Med. Chem. 46(2), (2003) 303-309.
Translation of Examiner Requirement in Mexican Application 2010008196 Apr. 30, 2012.

* cited by examiner

*Primary Examiner* — Rosalynd Keys
(74) *Attorney, Agent, or Firm* — Geroge W. Johnston; Patricia S. Rocha-Tramaloni; Gene J. Yao

(57) ABSTRACT

This invention relates to novel 4-dimethylaminobutyric acid derivatives of the formula

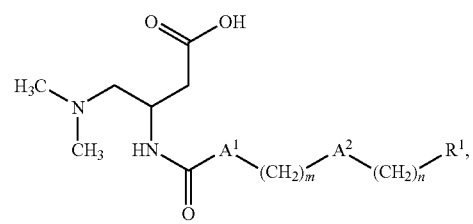

wherein $A^1$, $A^2$, $R^1$, m and n are as defined in the description and in the claims, as well as pharmaceutically acceptable salts thereof. These compounds inhibit carnitine palmitoyl transferase (CPT) activity, in particular CPT2 activity, and can be used as medicaments in methods for the treatment of diseases modulated by CPT2 inhibitors.

30 Claims, No Drawings

4-DIMETHYLAMINOBUTYRIC ACID DERIVATIVES

PRIORITY TO RELATED APPLICATION(S)

This application claims the benefit of European Patent Application No. 08155323.2, filed Apr. 29, 2008, which is hereby incorporated by reference in its entirety.

FIELD OF THE INVENTION

This invention is concerned with novel 4-dimethylaminobutyric acid derivatives, a process for the manufacture of these compounds, pharmaceutical preparations which contain such compounds as well as the use of these compounds for the production of medicaments.

SUMMARY OF THE INVENTION

More specifically, the invention relates to compounds of the formula

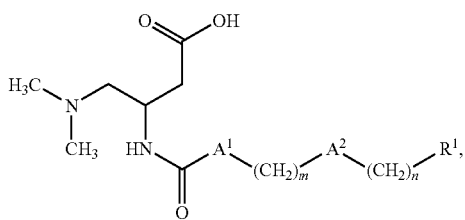

I wherein
$A^1$ is NH or a bond,
$A^2$ is selected from the group consisting of a bond, O, $O(CH_2)_2O$, S, $SO_2$, $CF_2$ and $NR^2$, wherein $R^2$ is hydrogen or lower alkyl,
m is selected from 2, 3, 4, 5, 6, 7, 8, 9, 10 and 11,
n is selected from 0, 1, 2, 3, 4 and 5,
$R^1$ is aryl selected from phenyl and naphthyl, said aryl being unsubstituted or substituted by one, two, three, four or five groups selected from the group consisting of lower alkyl, halogen, lower halogenalkyl, lower alkoxy and phenyl, or heteroaryl selected from the group consisting of pyridyl, thienyl and thiazolyl, said heteroaryl being unsubstituted or substituted by one, two or three groups selected from lower alkyl, halogen, lower halogenalkyl, lower alkoxy and phenyl,
and pharmaceutically acceptable salts thereof.

DETAILED DESCRIPTION

More specifically, the invention relates to compounds of the formula

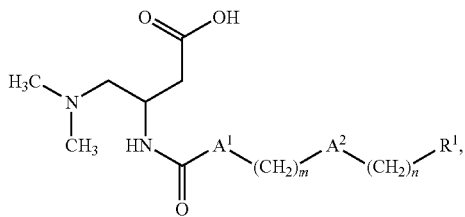

I wherein
$A^1$ is NH or a bond,
$A^2$ is selected from the group consisting of a bond, O, $O(CH_2)_2O$, S, $SO_2$, $CF_2$ and $NR^2$, wherein $R^2$ is hydrogen or lower alkyl,
m is selected from 2, 3, 4, 5, 6, 7, 8, 9, 10 and 11,
n is selected from 0, 1, 2, 3, 4 and 5,
$R^1$ is aryl selected from phenyl and naphthyl, said aryl being unsubstituted or substituted by one, two, three, four or five groups selected from the group consisting of lower alkyl, halogen, lower halogenalkyl, lower alkoxy and phenyl, or heteroaryl selected from the group consisting of pyridyl, thienyl and thiazolyl, said heteroaryl being unsubstituted or substituted by one, two or three groups selected from lower alkyl, halogen, lower halogenalkyl, lower alkoxy and phenyl,
and pharmaceutically acceptable salts thereof.

Elevated plasma levels of free fatty acids (FFAs) cause acute and long-term peripheral and hepatic insulin resistance. Increased plasma FFA levels and increase FFA oxidation are associated with type 2 diabetes. Hyperglycemia after an overnight fast is a major hallmark and an important diagnostic criterion of diabetes, and excessive gluconeogenesis is mainly responsible for the postabsorptive hyperglycemia in diabetic patients. High levels of free fatty acids (FFA) lead to an increase of liver mitochondrial β-oxidation, which results in increased concentrations of acetyl CoA. This provides increased energy (ATP) and reducing force (NADH) for gluconeogenesis. Increased acetyl CoA levels also stimulate gluconeogenesis by an allosteric activation of pyruvate carboxylase. Thereby, reduction of excessive liver β-oxidation, which is crucial to drive efficient gluconeogenesis, should lead to a reduction of fasting hyperglycemia in diabetic patients. The mitochondrial oxidation of long-chain FFA requires the intervention of two membrane-bound carnitine-dependent palmitoyltransferases (CPTs). CPT1, the outer mitochondrial membrane enzyme, catalyzes the formation of long-chain acylcarnitines. Liver (L-CPT1) and muscle (M-CPT1) CPT1 isoforms are encoded by two different genes and inhibited by malonyl-CoA. The N-terminal domain of L-CPT1 confers its lower sensitivity to malonyl CoA. CPT2, the inner mitochondrial membrane enzyme, reconverts long-chain acylcarnitines into long-chain acyl CoA esters. Long-chain acyl-CoAs are then β-oxidized to acetyl-CoA, which activates the pyruvate carboxylase and gluconeogenesis. According to the mechanism of action described above, pharmaceutically active substances which inhibit transport of long chain FFA though the inhibition of CPTs, reduce liver β-oxidation, consequently inhibit gluconeogenesis and therefore counteract hyperglycemia.

The present invention relates to novel compounds which inhibit carnitine palmitoyl transferase (CPT) activity, in particular/preferentially CPT2 activity. The compounds of the present invention can be used as pharmaceutically active agents, which are useful in the prevention and/or treatment of diseases which are modulated by CPT inhibitors, in particular/preferentially CPT2 inhibitors, particularly diseases which are related to hyperglycemia and/or glucose tolerance disorders. Such diseases include e.g. diabetes and associated pathologies, non insulin dependent diabetes mellitus (also referred to as diabetes type II), obesity, hypertension, insulin resistance syndrome, metabolic syndrome, hyperlipidemia, hypercholesterolemia, fatty liver disease, atherosclerosis, congestive heart failure and renal failure.

The novel compounds of the present invention exceed the compounds known in the art, inasmuch as they inhibit in particular or preferentially CPT2 activity. They are therefore

3 expected to have an enhanced therapeutic potential compared to the compounds already known in the art.

A. Definitions

Unless otherwise indicated, the following definitions are set forth to illustrate and define the meaning and scope of the various terms used to describe the invention herein.

In this specification the term "lower" is used to mean a group consisting of one to seven, preferably of one to four carbon atom(s).

The term "halogen" refers to fluorine, chlorine, bromine and iodine, with fluorine, chlorine and bromine being preferred.

The term "alkyl", alone or in combination with other groups, refers to a branched or straight-chain monovalent saturated aliphatic hydrocarbon radical of one to twenty carbon atoms, preferably one to sixteen carbon atoms, more preferably one to ten carbon atoms. The term "$C_{1-10}$-alkyl" refers to a branched or straight-chain monovalent saturated aliphatic hydrocarbon radical of one to ten carbon atoms, such as e.g. methyl, ethyl, n-propyl, isopropyl, n-butyl, s-butyl, t-butyl, pentyl, 1,1,3,3-tetramethyl-butyl and the like. Lower alkyl groups as described below also are preferred alkyl groups.

The term "lower alkyl" or "$C_1$-$C_7$-alkyl", alone or in combination with other groups, refers to a branched or straight-chain monovalent alkyl radical of one to seven carbon atoms, preferably one to four carbon atoms. This term is further exemplified by such radicals as methyl, ethyl, n-propyl, isopropyl, n-butyl, s-butyl, t-butyl and the like.

The term "lower halogenalkyl" or "halogen-$C_1$-$C_7$-alkyl" refers to lower alkyl groups as defined above wherein at least one of the hydrogen atoms of the lower alkyl group is replaced by a halogen atom, preferably fluoro or chloro, most preferably fluoro. Among the preferred lower halogenalkyl groups are trifluoromethyl, difluoromethyl, trifluoroethyl, 2,2-difluoroethyl, fluoromethyl and chloromethyl, with trifluoromethyl being especially preferred.

The term "alkoxy" or "lower alkoxy" refers to the group R'—O—, wherein R' is lower alkyl and the term "lower alkyl" has the previously given significance. Examples of lower alkoxy groups are e.g. methoxy, ethoxy, n-propoxy, isopropoxy, n-butoxy, isobutoxy, sec-butoxy and tert-butoxy, preferably methoxy and ethoxy and most preferred methoxy.

Compounds of formula (I) can form pharmaceutically acceptable salts. Compounds of formula (I) can form salts with bases. Examples of such salts are alkaline, earth-alkaline and ammonium salts such as e.g. Na—, K—, Ca— and trimethylammonium salt. Compounds of formula I can also form pharmaceutically acceptable acid addition salts. Examples of such pharmaceutically acceptable salts are salts of compounds of formula (I) with physiologically compatible mineral acids, such as hydrochloric acid, sulphuric acid or phosphoric acid; or with organic acids, such as methanesulphonic acid, p-toluenesulphonic acid, acetic acid, lactic acid, citric acid, fumaric acid, maleic acid, tartaric acid, succinic acid or salicylic acid. The term "pharmaceutically acceptable salts" refers to all these salts.

B. Detailed Description

In detail, the present invention relates to compounds of the formula

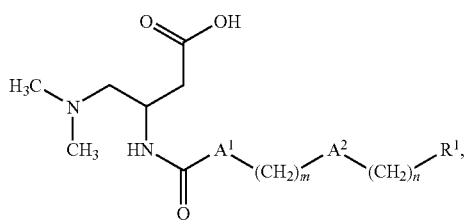

wherein
$A^1$ is NH or a bond,
$A^2$ is selected from the group consisting of a bond, O, $O(CH_2)_2 O$, S, $SO_2$, $CF_2$ and $NR^2$, wherein $R^2$ is hydrogen or lower alkyl,
m is selected from 2, 3, 4, 5, 6, 7, 8, 9, 10 and 11,
n is selected from 0, 1, 2, 3, 4 and 5,
$R^1$ is aryl selected from phenyl and naphthyl, said aryl being unsubstituted or substituted by one, two, three, four or five groups selected from the group consisting of lower alkyl, halogen, lower halogenalkyl, lower alkoxy and phenyl, or heteroaryl selected from the group consisting of pyridyl, thienyl and thiazolyl, said heteroaryl being unsubstituted or substituted by one, two or three groups selected from lower alkyl, halogen, lower halogenalkyl, lower alkoxy and phenyl,
and pharmaceutically acceptable salts thereof.

Compounds of formula I are individually preferred and pharmaceutically acceptable salts thereof are individually preferred, with the compounds of formula I being particularly preferred.

Preferred are further compounds of formula I according to the invention, wherein $A^1$ is a bond.

Furthermore, compounds of formula I according to the present invention are preferred, wherein $A^2$ is selected from the group consisting of a bond, O, $O(CH_2)_2O$, S, $SO_2$ and $NR^2$, wherein $R^2$ is hydrogen or lower alkyl.

More preferably, $A^2$ is selected from the group consisting of a bond, 0 and $O(CH_2)_2O$.

A group of more preferred compounds of formula I are those, wherein $A^2$ is O or $O(CH_2)_2O$, with those compounds of formula I being especially preferred, wherein $A^2$ is O (oxygen).

Another group of preferred compounds of formula I are those, wherein $A^2$ is a bond.

Preferred are further compounds of formula I according to the present invention, wherein m is selected from 6, 7, 8, 9, 10 and 11.

Further preferred are compounds of formula I according to the invention, wherein n is selected from 0, 1, 2 and 3, with those compounds being more preferred, wherein n is selected from O or 1, and those being most preferred wherein n is 1.

Especially preferred are compounds of formula I, wherein the sum of m and n is selected from 8, 9 and 10.

A group of preferred compounds of formula (I) according to the invention are further those, wherein $R^1$ is aryl selected from phenyl and naphthyl, said aryl being unsubstituted or substituted by one, two, three, four or five groups selected from the group consisting of lower alkyl, halogen, lower halogenalkyl, lower alkoxy and phenyl.

Especially preferred are compounds of formula I according to the invention, wherein $R^1$ is phenyl substituted by one, two, three, four or five groups selected from the group consisting of lower alkyl, halogen, lower halogenalkyl, lower alkoxy and phenyl. More preferred are those compounds of formula I, wherein $R^1$ is phenyl substituted by one, two, three, four or five groups selected from the group consisting of lower alkyl, halogen, lower halogenalkyl, lower alkoxy and phenyl provided that at least one of the substituents is halogen or lower halogenalkyl. Especially preferred $R^1$ is phenyl substituted by one, two, three, four or five groups selected from halogen and lower halogenalkyl.

Another group of preferred compounds of formula I according to the present invention are those, wherein $R^1$ is heteroaryl selected from the group consisting of pyridyl, thienyl and thiazolyl, said heteroaryl being unsubstituted or substituted by one, two or three groups selected from lower alkyl, halogen, lower halogenalkyl, lower alkoxy and phenyl.

Especially preferred are compounds of formula I of the invention, wherein $R^1$ is heteroaryl selected from the group consisting of pyridyl, thienyl and thiazolyl.

Furthermore, compounds of formula I having (R)-configuration are especially preferred, i.e. these are the compounds having the formula

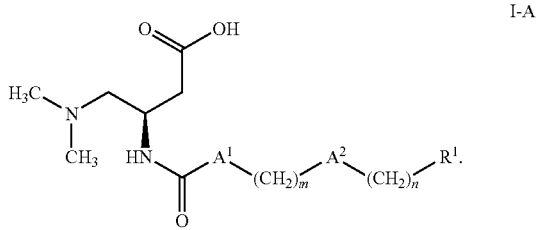

I-A

Preferred compounds of formula I are those selected from the group consisting of:
(R)-3-[8-(3,4-difluoro-benzyloxy)-octanoylamino]-4-dimethylamino-butyric acid,
(R)-3-[8-(2,5-difluoro-benzyloxy)-octanoylamino]-4-dimethylamino-butyric acid,
(R)-3-[8-(2,4-difluoro-benzyloxy)-octanoylamino]-4-dimethylamino-butyric acid,
(R)-4-dimethylamino-3-[8-(2,3,4-trifluoro-benzyloxy)-octanoylamino]-butyric acid,
(R)-4-dimethylamino-3-(8-pentafluorophenylmethoxy-octanoylamino)-butyric acid,
(R)-4-dimethylamino-3-[8-(4-trifluoromethyl-benzyloxy)-octanoylamino]-butyric acid,
(R)-4-dimethylamino-3-[8-(3-fluoro-4-trifluoromethyl-benzyloxy)-octanoylamino]-butyric acid,
(R)-4-dimethylamino-3-[8-(4-methoxy-benzyloxy)-octanoylamino]-butyric acid,
(R)-3-[8-(biphenyl-4-ylmethoxy)-octanoylamino]-4-dimethylamino-butyric acid,
(R)-4-dimethylamino-3-[8-(2-fluoro-4-trifluoromethyl-benzyloxy)-octanoylamino]-butyric acid,
(R)-4-dimethylamino-3-[8-(2,3,5,6-tetrafluoro-4-methoxy-benzyloxy)-octanoylamino]-butyric acid,
(R)-4-dimethylamino-3-[8-(naphthalen-1-ylmethoxy)-octanoylamino]-butyric acid,
(R)-4-dimethylamino-3-[8-(2-fluoro-benzyloxy)-octanoylamino]-butyric acid,
(R)-4-dimethylamino-3-[8-(3-fluoro-benzyloxy)-octanoylamino]-butyric acid,
(R)-4-dimethylamino-3-[8-(4-fluoro-benzyloxy)-octanoylamino]-butyric acid,
(R)-3-[8-(2,3-difluoro-benzyloxy)-octanoylamino]-4-dimethylamino-butyric acid,
(R)-3-(8-benzyloxy-octanoylamino)-4-dimethylamino-butyric acid,
(R)-4-dimethylamino-3-[9-(2-fluoro-phenoxy)-nonanoylamino]-butyric acid,
(R)-4-dimethylamino-3-[9-(3-fluoro-phenoxy)-nonanoylamino]-butyric acid,
(R)-4-dimethylamino-3-[9-(4-fluoro-phenoxy)-nonanoylamino]-butyric acid,
(R)-3-[9-(2,3-difluoro-phenoxy)-nonanoylamino]-4-dimethylamino-butyric acid,
(R)-3-[9-(2,4-difluoro-phenoxy)-nonanoylamino]-4-dimethylamino-butyric acid,
(R)-3-[9-(3,4-difluoro-phenoxy)-nonanoylamino]-4-dimethylamino-butyric acid,
(R)-4-dimethylamino-3-[9-(2,3,4-trifluoro-phenoxy)-nonanoylamino]-butyric acid,
(R)-3-[9-(biphenyl-4-yloxy)-nonanoylamino]-4-dimethylamino-butyric acid,
(R)-3-[9-(3,4-dimethoxy-phenoxy)-nonanoylamino]-4-dimethylamino-butyric acid,
(R)-4-dimethylamino-3-[9-(4-trifluoromethyl-phenoxy)-nonanoylamino]-butyric acid,
(R)-4-dimethylamino-3-[9-(4-methoxy-phenoxy)-nonanoylamino]-butyric acid,
(R)-4-dimethylamino-3-[9-(naphthalen-1-yloxy)-nonanoylamino]-butyric acid,
(R)-4-dimethylamino-3-(11-phenoxy-undecanoylamino)-butyric acid,
(R)-4-dimethylamino-3-(9-phenoxy-nonanoylamino)-butyric acid,
(R)-4-dimethylamino-3-(10-phenyl-decanoylamino)-butyric acid,
(S)-4-dimethylamino-3-(10-phenyl-decanoylamino)-butyric acid,
(R)-4-dimethylamino-3-[10-(4-fluoro-phenyl)-decanoylamino]-butyric acid,
(R)-4-dimethylamino-3-[10-(2-fluoro-phenyl)-decanoylamino]-butyric acid,
(R)-4-dimethylamino-3-[10-(2,5-dimethyl-phenyl)-decanoylamino]-butyric acid,
(R)-4-dimethylamino-3-[10-(2,6-dimethyl-phenyl)-decanoylamino]-butyric acid,
(R)-4-dimethylamino-3-[10-(4-methoxy-phenyl)-decanoylamino]-butyric acid,
(R)-4-dimethylamino-3-(10-naphthalen-1-yl-decanoylamino)-butyric acid,
(R)-4-dimethylamino-3-[10-(4-trifluoromethyl-phenyl)-decanoylamino]-butyric acid,
(R)-4-dimethylamino-3-[10-(3-fluoro-phenyl)-decanoylamino]-butyric acid,
(R)-3-[10-(2,3-difluoro-phenyl)-decanoylamino]-4-dimethylamino-butyric acid,
(R)-4-dimethylamino-3-(10-thiophen-3-yl-decanoylamino)-butyric acid,
(R)-4-dimethylamino-3-(10-thiazol-5-yl-decanoylamino)-butyric acid,
(R)-4-dimethylamino-3-(6-phenyl-hexanoylamino)-butyric acid,
(R)-4-dimethylamino-3-(7-phenyl-heptanoylamino)-butyric acid,
(R)-4-dimethylamino-3-(8-phenyl-octanoylamino)-butyric acid, (R)-4-dimethylamino-3-(9-phenyl-nonanoylamino)-butyric acid,
(R)-4-dimethylamino-3-(9-pyridin-3-yl-nonanoylamino)-butyric acid,
(R)-4-dimethylamino-3-(11-phenyl-undecanoylamino)-butyric acid,
(R)-4-dimethylamino-3-(12-phenyl-dodecanoylamino)-butyric acid,
(R)-4-dimethylamino-3-[4-(5-phenyl-pentyloxy)-butyrylamino]-butyric acid,
(R)-4-dimethylamino-3-[6-(3-phenyl-propoxy)-hexanoylamino]-butyric acid,
(R)-4-dimethylamino-3-(9-phenethyloxy-nonanoylamino)-butyric acid,
(R)-4-dimethylamino-3-[8-(3-phenyl-propoxy)-octanoylamino]-butyric acid,
(R)-4-dimethylamino-3-[8-(2-phenoxy-ethoxy)-octanoylamino]-butyric acid,
(R)-3-(10-benzyloxy-decanoylamino)-4-dimethylamino-butyric acid,
(R)-4-dimethylamino-3-[7-(2-phenyl-ethanesulfonyl)-heptanoylamino]-butyric acid,
(R)-4-dimethylamino-3-(8-(phenylmethanesulfonyl)-octanoylamino)-butyric acid,
(R)-3-(9-benzenesulfonyl-nonanoylamino)-4-dimethylamino-butyric acid,
(R)-3-{7-[2-(2,3-difluoro-phenyl)-ethoxy]-heptanoylamino}-4-dimethylamino-butyric acid,
(R)-3-{3-[6-(2,3-difluoro-benzyloxy)-hexyl]-ureido}-4-dimethylamino-butyric acid,
(R)-4-dimethylamino-3-[3-(9-phenyl-nonyl)-ureido]-butyric acid,
(R)-4-dimethylamino-3-[9-(methyl-phenethyl-amino)-nonanoylamino]-butyric acid,
(R)-4-dimethylamino-3-(9-phenethylamino-nonanoylamino)-butyric acid,
(R)-4-dimethylamino-3-[9-(methyl-phenyl-amino)-nonanoylamino]-butyric acid,
and pharmaceutically acceptable salts thereof.

Particularly preferred compounds of formula I are those selected from the group consisting of:
(R)-4-dimethylamino-3-[8-(4-trifluoromethyl-benzyloxy)-octanoylamino]-butyric acid,
(R)-3-[8-(biphenyl-4-ylmethoxy)-octanoylamino]-4-dimethylamino-butyric acid,
(R)-4-dimethylamino-3-[9-(3-fluoro-phenoxy)-nonanoylamino]-butyric acid,
(R)-4-dimethylamino-3-[9-(4-fluoro-phenoxy)-nonanoylamino]-butyric acid,
(R)-3-[9-(3,4-difluoro-phenoxy)-nonanoylamino]-4-dimethylamino-butyric acid,
(R)-4-dimethylamino-3-[9-(2,3,4-trifluoro-phenoxy)-nonanoylamino]-butyric acid,
(R)-4-dimethylamino-3-[9-(naphthalen-1-yloxy)-nonanoylamino]-butyric acid,
(R)-4-dimethylamino-3-(10-phenyl-decanoylamino)-butyric acid,
(R)-4-dimethylamino-3-[10-(2-fluoro-phenyl)-decanoylamino]-butyric acid,
(R)-4-dimethylamino-3-(10-naphthalen-1-yl-decanoylamino)-butyric acid,
(R)-4-dimethylamino-3-[10-(4-trifluoromethyl-phenyl)-decanoylamino]-butyric acid,
(R)-3-[10-(2,3-difluoro-phenyl)-decanoylamino]-4-dimethylamino-butyric acid,
(R)-4-dimethylamino-3-(10-thiophen-3-yl-decanoylamino)-butyric acid,
(R)-4-dimethylamino-3-(9-phenethyloxy-nonanoylamino)-butyric acid,
(R)-4-dimethylamino-3-[8-(2-phenoxy-ethoxy)-octanoylamino]-butyric acid,
and pharmaceutically acceptable salts thereof.

Especially preferred is a compound of formula I, which is (R)-4-dimethylamino-3-(10-phenyl-decanoylamino)-butyric acid.

It will be appreciated that the compounds of general formula I in this invention may be derivatised at functional groups to provide derivatives which are capable of conversion back to the parent compound in vivo.

The invention also relates to a process for the preparation of compounds of formula I as defined above, which process comprises
a) condensating an amine of formula

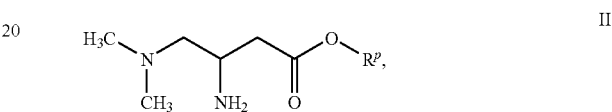

wherein $R^p$ is methyl, ethyl or benzyl, with a carboxylic acid of the formula

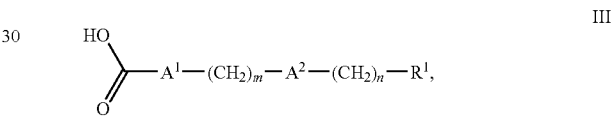

wherein $A^1$ is a bond and $A^2$, m, n and R' are as defined herein before, in the presence of a base and a condensing agent to obtain a compound of the formula

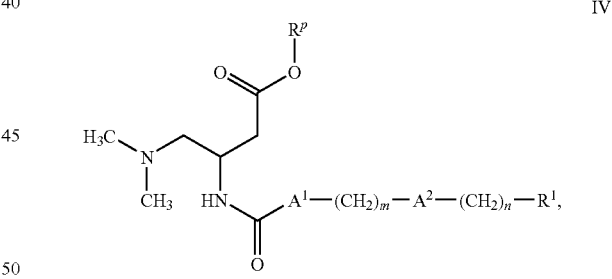

and transforming the compound of formula IV into a compound of formula I, wherein $A^1$ is a bond, by ester hydrolysis or hydrogenation, or
b) condensating the amine of formula

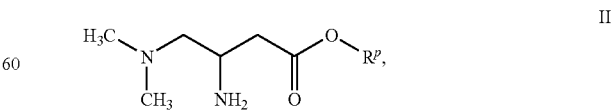

wherein $R^1$ is methyl, ethyl or benzyl, with an isocyanate of the formula

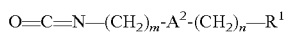

wherein $A^2$, m, n and $R^1$ are as defined herein before, in the presence of a base to obtain a compound of the formula

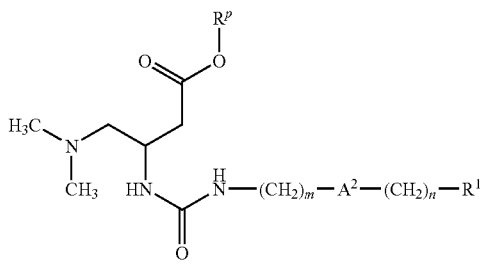

VI and transforming the compound of formula VI into a compound of formula I, wherein $A^1$ is NH, by ester hydrolysis or hydrogenation, or c) condensating the amine of formula

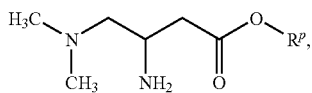

II wherein $R^1$ is benzyl, with a carboxylic acid of the formula

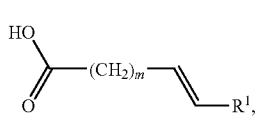

VII wherein m and $R^1$ are as defined herein before, in the presence of a base and a condensing agent to obtain a compound of the formula

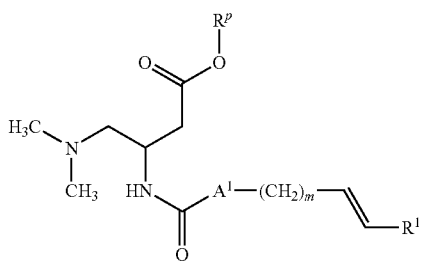

VIII and transforming the compound of formula VIII into a compound of formula I, wherein $A^2$ is a bond and n is 2, by hydrogenation.

Ester hydrolysis means a base-catalyzed hydrolysis using reagents such as lithium hydroxide, sodium hydroxide, potassium hydroxide, in solvents such as water, methanol, ethanol, tetrahydrofuran, or mixtures thereof, at temperatures between 0° C. and 100° C. Hydrogenation is normally carried out at a hydrogen pressure of 1 to 10 bar, using a suitable catalyst such as palladium on activated charcoal, in a solvent such as methanol or ethanol, at a temperature between 0° C. and 50° C., but hydrogenation can also mean reduction of a double bond using triethysilane and trifluoroacetic acid in an inert solvent such as toluene or dichloromethane followed by ester hydrolysis as described hereinbefore.

As compounds of formula I having (R)-configuration are preferred, the 3-amino-4-dimethylaminobutyrate of the formula

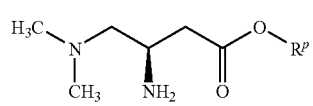

II-A is preferably used in the processes of the present invention.

The present invention also relates to compounds of formula I as defined above, when prepared by a process as described above.

In more detail, the compounds of formula I are synthesized from the corresponding esters 1 ($R^p$=methyl, ethyl, benzyl), using methods known in the art. Especially preferred are compounds 1 with $R^p$=benzyl, which can be converted to 1 by hydrogenation at a pressure of 1-10 bar, using a suitable catalyst, e.g., palladium on activated charcoal, in a solvent such as methanol or ethanol, at 0 to 50° C. Alternatively, esters 1 can be transformed into compounds of formula I by base-catalyzed hydrolysis, using reagents such as lithium hydroxide, sodium hydroxide, potassium hydroxide, in solvents such as water, methanol, ethanol, tetrahydrofuran, or mixtures thereof, at temperatures between 0° C. and 100° C.

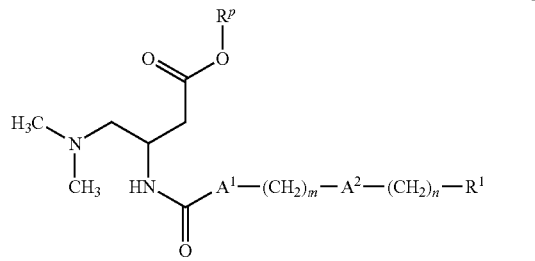

1

Alternatively, compounds of formula I, wherein $A^2$ is a bond and n is 2, can also be synthesized from ester 2 (in the case where $R^p$ is benzyl) by hydrogenation as described above, whereby a double bond eventually adjacent to $R^1$ as a result of the synthetic protocol used (see below) is also reduced. In the case where $R^p$ is methyl, ethyl, or benzyl, the transformation of 2 into a compound of formula I can also be accomplished in two steps as follows: In a first step the aforementioned double bond is reduced using triethysilane and trifluoroacetic acid in an inert solvent such as toluene or dichloromethane. In the second step the ester group is hydrolyzed, using reagents such as lithium hydroxide, sodium hydroxide, potassium hydroxide, in solvents such as water, methanol, ethanol, tetrahydrofuran, or mixtures thereof, at temperatures between 0° C. and 100° C.

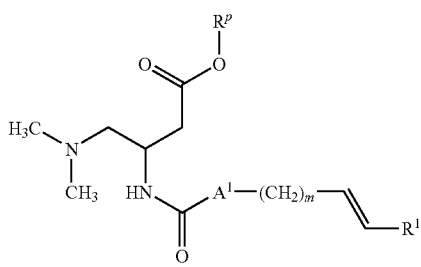

2

Compounds of formula 1 where $A^1$ is NH can be synthesized from 3-amino-4-dimethylaminobutyrate 3

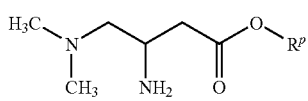

3 and isocyanate 4.

O=C=N—(CH$_2$)$_m$-A$^2$-(CH$_2$)$_n$—R$^1$     4

The reaction is preferably accomplished in an aprotic solvent such as dichloromethane or tetrahydrofuran, optionally in the presence of a base, e.g., triethylamine or 4-methylmorpholine.

Compounds of formula 1 where $A^1$ is a bond are synthesized from 3-amino-4-dimethylaminobutyrate 3 and carboxylic acid 5.

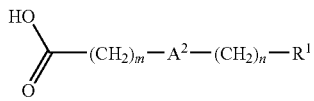

5

This can be carried out under conditions well known to the person skilled in the art. Such reactions can conveniently be carried out for example by mixing carboxylic acid 5 with amine 3 in aprotic solvents such as dichloromethane, tetrahydrofuran, N,N-dimethylformamide, N-methylpyrrolidinone and mixtures thereof at temperatures between 0° C. and 60° C. in the presence or absence of a base such as triethylamine or N,N-diisopropylethylamine, and a condensing agent. Appropriate condensing agents can be for example O-(7-benzotriazol-1-yl)-N,N,N',N'-tetramethyluronium-tetrafluoroborate (TBTU), O-(7-azabenzotriazol-1-yl)-N,N,N',N'-tetramethyluronium-hexaflurophophate (HATU), N,N'-dicyclohexylcarbodiimide, 1-(3-dimethylaminopropyl)-3-ethyl-carbodiimide hydrochloride, O-(benzotriazol-1-yl)-N,N,N',N'-tetramethyluronium hexafluoro-phosphate, bromo-tris-pyrrolidino-phosphonium hexafluorophosphate or others well known to the person skilled in the art.

Alternatively, such reactions can be performed in two steps involving first formation of the acyl halide derivative of 5 and subsequent coupling reaction with amine 3 in the presence of a base. Typically employed reagents for the formation of the acyl chloride are thionyl chloride, phosphorus pentachloride, oxalyl chloride or cyanuric chloride, and the reaction is generally conducted in the absence of a solvent or in the presence of an aprotic solvent like dichloromethane, toluene or acetone. A base can optionally be added, like for example pyridine, triethylamine, N,N-diisopropylethylamine or 4-methylmorpholine. The obtained acyl chloride can be isolated or reacted as such with an amine 3 in an aprotic solvent, like dichloromethane, tetrahydrofuran or acetone, in the presence of a base. Typical bases are triethylamine, 4-methylmorpholine, pyridine, N,N-diisopropylethyl-amine or dimethylaminopyridine or mixtures thereof.

Alternatively, such reactions can be performed in two steps involving first formation of a mixed anhydride derivative of 5 obtained by reaction with a reagent such as ethyl chloroformate, isobutyl chloroformate, or acetic anhydride, and subsequent reaction with amine 3 as described above.

Compounds of formula 2 are synthesized from 3-amino-4-dimethylaminobutyrate 3 and carboxylic acid 6, in analogy to 1.

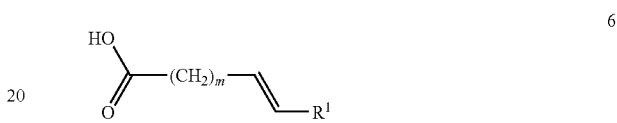

6

The synthesis of 3-amino-4-dimethylaminobutyrate 3 is highlighted in scheme 1 and starts from commercially available N-protected aspartic acid monoester 7. R$^p$ is methyl, ethyl, or benzyl, with benzyl being especially preferred.

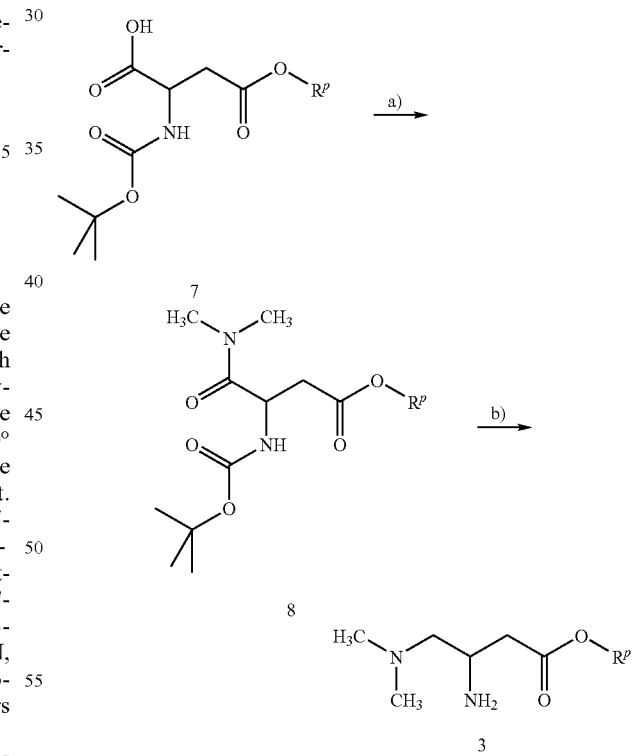

In step a, scheme 1, carboxylic acid 7 is reacted with dimethylamine to the N,N-dimethylamide derivative 8, using reagents and methods as described for the reaction of carboxylic acid 5 with amine 3. In step b, scheme 1, N,N-dimethylamide 8 is converted to dimethylamine derivative 3 by reduction and subsequent removal of the tert-butoxycarbonyl protective group. Preferred reagents for the reduction are borane-tetrahydrofuran complex or borane-dimethylsulfide complex, in an aprotic solvent such as tetrahydrofuran, at temperature between −20° C. and 80° C. Removal of the tert-butoxycarbonyl group is accomplished in an acidic environment, using hydrochloric acid or sulfuric acid, in solvents such as ethanol, methanol, water or mixtures thereof, at temperatures between 0° C. and 20° C.

Isocyanate 4 is synthesized from carboxylic acid 5 as highlighted in scheme 2. This conversion is accomplished by methods well known in the art, e.g., Curtius rearrangement. A typical procedure starts the transformation of 5 to its acyl halide derivative. Typically employed reagents for the formation of the acyl chloride are thionyl chloride, phosphorus pentachloride, oxalyl chloride, ethyl chloroformate, isobutyl chloroformate, or cyanuric chloride, and the reaction is generally conducted in the absence of a solvent or in the presence of an aprotic solvent like dichloromethane or toluene. A base can optionally be added, like for example pyridine, triethylamine, diisopropyl ethyl amine or 4-methylmorpholine. The obtained acyl chloride can be isolated or reacted as such with sodium azide, leading to the acyl azide derivative of 5, which is not isolated but heated to >60° C., whereupon it rearranges to isocyanate 4 under elimination of nitrogen gas.

Scheme 2

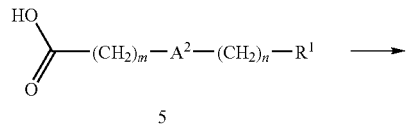

5

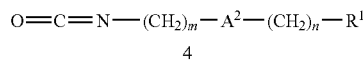

4

Alternatively, the conversion of 5 to 4 can be accomplished in a single step, using diphenylphosphoryl azide as azide source, optionally in the presence of a base, e.g., triethylamine, at temperatures between 0° C. and 110° C., preferably in toluene.

Carboxylic acids 5 are either commercially available or can be produced as outlined in schemes 3 to 10.

When $R^1$ is as described above, $A^2$ is O, O(CH$_2$)$_2$O, S or SO$_2$, the carboxylic acids 5 can be produced as described in scheme 3, where X is a leaving group such as bromine, iodine, or methanesulfonyloxy and PG is an optional protective group, e.g., tetrahydropyran-2-yl.

Scheme 3

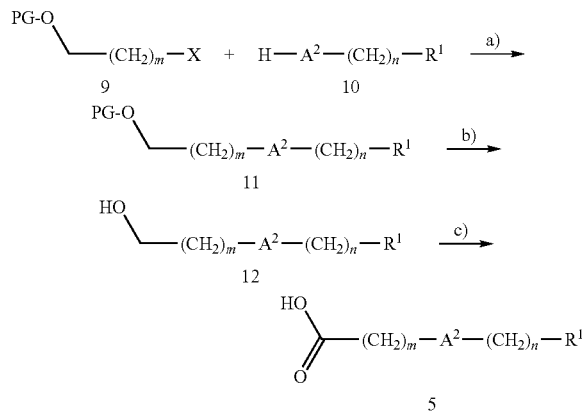

In step a, scheme 3, compound 10 is alkylated with optionally protected ω-halo or ω-sulfonyloxy alcohol 9, leading to 11. The reaction is performed in a solvent such as ethanol, acetonitrile, or N,N-dimethylformamide, in the presence of a base, e.g., potassium carbonate, sodium hydroxide, potassium tert-butylate, or sodium hydride, at temperatures between 0° C. and 100° C.

In optional step b (i e., in the case where PG≠H), the protective group of 11 is removed, leading to alcohol 12. In the case of PG=tetrahydropyran-2-yl, this reaction is accomplished using an acid catalyst such as hydrochloric acid, toluene-4-sulfonic acid, or pyridinium toluene-4-sulfonate, in a solvent such as water, methanol, or ethanol, at temperatures between 0° C. and 100° C.

In step c, scheme 3, alcohol 12 is oxidized to carboxylic acid 5. Typically employed reagents and conditions for the oxidation of alcohol 12 include pyridinium dichromate, chromium(VI)oxide, or potassium permanganate. This oxidation of 12 to 5 is also possible for alcohols 12 in which $A^2$ is a bond.

Alternatively, alcohol 12 can be synthesized as outlined in scheme 4. $A^2$ is oxygen, sulfur, or SO$_2$, $R^1$, m and n are as defined above. In this route diol 13 and compound 14 are reacted under Mitsunobu conditions using a phosphine, e.g., triphenylphosphine, and an azodicarboxylic acid diester, e.g., diethyl azodicarboxylate or diisopropyl azodicarboxylate, in a solvent such as tetrahydrofuran, dichloromethane, or toluene, at temperatures between 0° C. and 50° C., leading to 12.

Scheme 4

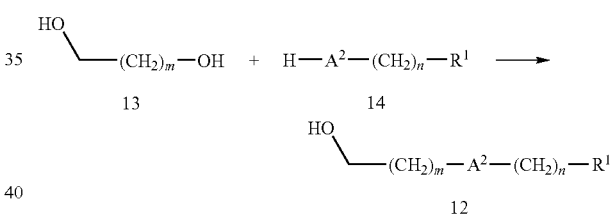

Alternatively, alcohol 12 can be synthesized as outlined in scheme 5. In this case $A^2$ is O, S or SO$_2$, $R^1$, m and n are as defined above and X is a leaving group such as bromine, iodine, or methanesulfonyloxy. Thus, compound 15 is alkylated with halide or sulfonate 16. The reaction is performed in a solvent such as ethanol, acetonitrile, or N,N-dimethylformamide, in the presence of a base, e.g., potassium carbonate, sodium hydroxide, potassium tert-butylate, or sodium hydride, at temperatures between 0° C. and 100° C.

Scheme 5

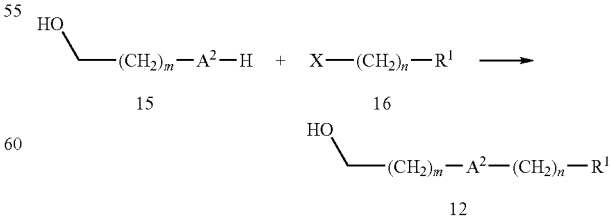

Acid 5 can also be synthesized as outlined in scheme 6. In this case $A^2$ is O, S or SO$_2$, $R^1$, m and n are as defined above, X is a leaving group such as bromine, iodine, or methanesulfonyloxy. The alkylation of carboxylic acid 17 with halide or sulfonate 16 is performed in an analogous fashion to that of 16 with 17 (scheme 5).

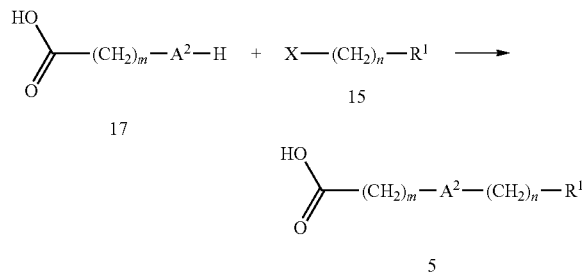

Scheme 6

Acid 5, in which $A^2$ is $N(R^2)$, is represented as a compound of formula 18. The compound of formula 18 can be synthesized as outlined in scheme 7. $R^1$, $R^2$, m and n are as defined above.

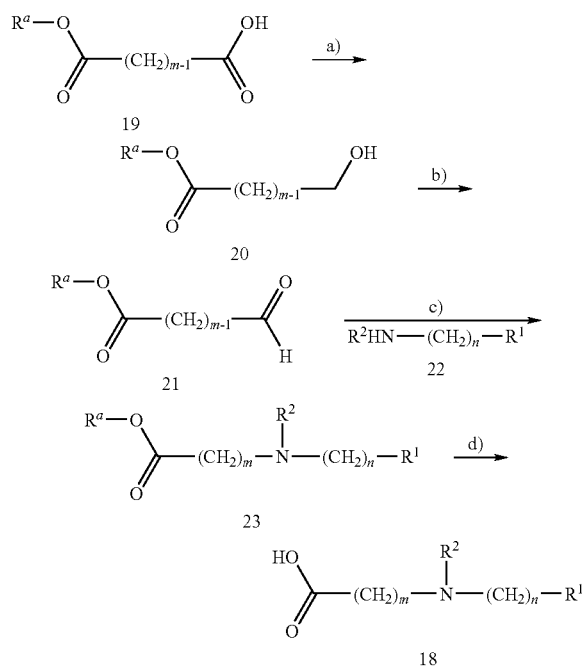

Scheme 7

In step a, scheme 7, dicarboxylic acid monoester 19 is reduced to ω-hydroxyester 20, using reagents known in the art, e.g., borane-tetrahydrofuran complex, in a solvent such as tetrahydrofuran, at temperatures between 0° C. and 50° C.

In step b, scheme 7, the hydroxy group of 20 is oxidized to a formyl group, leading to 21. Suitable reagents are e.g., sodium hypochlorite, in the presence of potassium bromide, 2,2,6,6-tetramethylpiperidin-1-oxyl, and sodium hydrogencarbonate, in a biphasic mixture of water and dichloromethane, at around 0° C. Alternatively dimethyl sulfoxide-based reagents can be employed, such as dimethyl sulfoxide—oxalyl chloride, or dimethyl sulfoxide—trifluoroacetic anhydride, in a solvent such as dichloromethane, at temperatures below 0° C., typically at −78° C.

In step c, scheme 7, aldehyde 21 is reacted with amine 22 in the presence of a reducing agent to give aminoester 23. Typically used reagents are sodium borohydride (optionally in the presence of titanium(IV)isopropoxide), sodium cyanoborohydride, or sodium triacetoxyborohydride, in solvents such as methanol, acetic acid, tetrahydrofuran, 1,2-dichloroethane, or mixtures thereof, at temperatures between 0° C. and 100° C.

In step d, scheme 7, aminoester 23 is converted to acid 18 by base-catalyzed hydrolysis, using reagents such as lithium hydroxide, sodium hydroxide, potassium hydroxide, in solvents such as water, methanol, ethanol, tetrahydrofuran, or mixtures thereof, at temperatures between 0° C. and 100° C.

Alternatively, aminoester 23 can be accessed as outlined in scheme 8. $R^1$, $R^2$ and m are as defined above, $R^a$ is lower alkyl, e.g., methyl or ethyl.

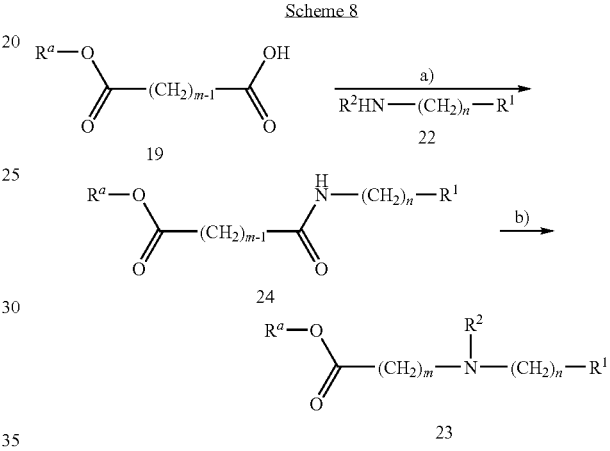

Scheme 8

In step a, scheme 8, amide 24 is obtained from acid 19 by treatment with amine 22, using reagents and methods as described for the reaction of carboxylic acid 5 with amine 3.

In step b, scheme 8, aminoester 23 is obtained by reduction of amide 24, using reagents such as diborane, borane-dimethylsulfide complex or borane-tetrahydrofuran complex in solvents such as tetrahydrofuran at temperatures between 0° C. and 100° C.

Unsaturated acids of general formula 6 can be synthesized as outlined in scheme 9. $R^1$ and m are as defined above, $R^a$ is lower alkyl, e.g., methyl or ethyl.

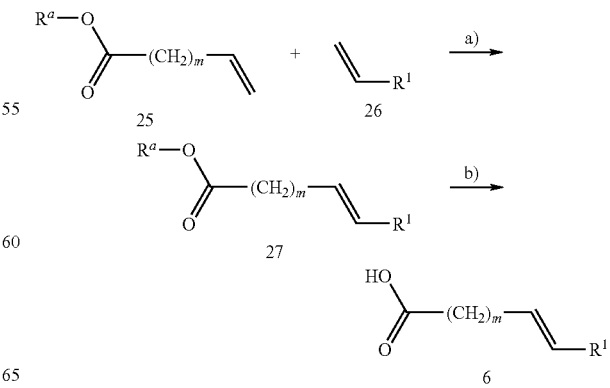

Scheme 9

In step a, scheme 9, unsaturated ester 25 is reacted with styrene derivative 26 in an alkene cross-metathesis reaction, leading to 27. This reaction is carried out in an inert solvent, such as dichloromethane or toluene and requires a suitable catalyst, e.g., dichloro(1,3-dimesityl-4,5-dihydroimidazol-2-ylidene)(phenylmethylene)(tricyclohexyl-phosphine)ruthenium, at temperatures between 20° C. and 100° C.

In step b, scheme 9, ester 27 is converted to acid 6 by base-catalyzed hydrolysis, in analogy to scheme 7, step d.

Alternatively, unsaturated acids of formula 6 can be synthesized as outlined in scheme 10. $R^1$ and m are as defined above.

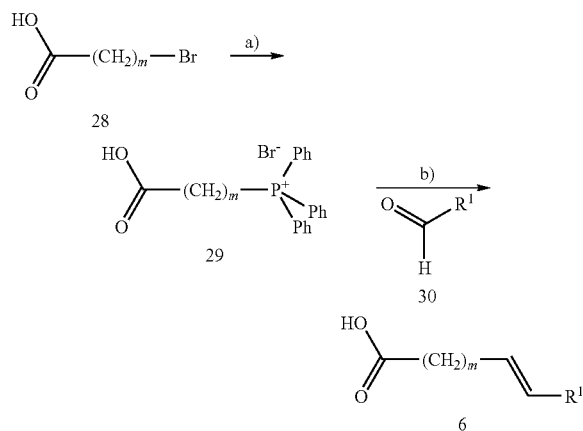

Scheme 10

In step a, scheme 10, ω-bromoacid 28 is reacted with triphenylphosphine, leading to phosphonium salt 29. This reaction is carried out in an inert solvent such as toluene, at temperatures between 20° C. and 110° C.

In step b, scheme 10, phosphonium salt 29 is reacted with aldehyde 30, leading to 6. This reaction is carried out in the presence of a base, e.g., sodium hydride, n-butyllithium, or potassium tert-butylate, in a solvent such as diethyl ether or tetrahydrofuran, at temperatures between −20° C. and 50° C.

As described above, the novel compounds of formula I of the present invention have been found to inhibit carnitine palmitoyl transferase 2 (CPT2) activity. The compounds of the present invention can therefore be used in the treatment and/or prophylaxis of diseases that are modulated by CPT2 inhibitors, particularly diseases that are related to hyperglycemia and/or glucose tolerance disorders. Such diseases include e.g. diabetes and associated pathologies, non insulin dependent diabetes mellitus, obesity, hypertension, insulin resistance syndrome, metabolic syndrome, hyperlipidemia, hypercholesterolemia, fatty liver disease, atherosclerosis, congestive heart failure and renal failure.

The invention therefore also relates to pharmaceutical compositions comprising a compound of formula I as defined above and a pharmaceutically acceptable carrier and/or adjuvant.

The invention also embraces compounds of formula I as described above for use as therapeutically active substances, especially as therapeutically active substances for the treatment and/or prophylaxis of diseases which are modulated by CPT2 inhibitors, particularly for use as therapeutically active substances for the treatment and/or prophylaxis of hyperglycemia, glucose tolerance disorders, diabetes and associated pathologies, non insulin dependent diabetes mellitus, obesity, hypertension, insulin resistance syndrome, metabolic syndrome, hyperlipidemia, hypercholesterolemia, fatty liver disease, atherosclerosis, congestive heart failure and renal failure.

In another preferred embodiment, the invention relates to a method for the therapeutic and/or prophylactic treatment of diseases which are modulated by CPT2 inhibitors, particularly for the therapeutic and/or prophylactic treatment of hyperglycemia, glucose tolerance disorders, diabetes and associated pathologies, non insulin dependent diabetes mellitus, obesity, hypertension, insulin resistance syndrome, metabolic syndrome, hyperlipidemia, hypercholesterolemia, fatty liver disease, atherosclerosis, congestive heart failure and renal failure, which method comprises administering a compound of formula I as defined above to a human being or animal.

The invention also relates to the use of compounds of formula I as described above for the preparation of medicaments for the therapeutic and/or prophylactic treatment of diseases which are modulated by CPT2 inhibitors, particularly for the therapeutic and/or prophylactic treatment of hyperglycemia, glucose tolerance disorders, diabetes and associated pathologies, non insulin dependent diabetes mellitus, obesity, hypertension, insulin resistance syndrome, metabolic syndrome, hyperlipidemia, hypercholesterolemia, fatty liver disease, atherosclerosis, congestive heart failure and renal failure. Such medicaments comprise a compound of formula I as described above.

Prevention and/or treatment of hyperglycemia and non insulin dependent diabetes mellitus is the preferred use.

The following tests were carried out in order to determine the activity of the compounds of the present invention. Background information on the performed assays can be found in: Jackson et al., 1999, *Biochem. J.* 341, 483-489 and Jackson et al., 2000, *J. Biol. Chem.* 275, 19560-19566.

Human and rat CPT2- and liver CPT1 cDNAs, and human muscle CPT1 cDNA were subcloned in pGAPZB or pGAPZA, respectively. These plasmids were used to transform *P. pastoris* strain X-33 via electroporation after the preparation of electrocompetent cells. High copy number clones were selected where necessary using 0.5 or 1 mg/ml Zeocin. Cultures for activity measurements were induced for 16 h in YPD medium (1% yeast extract, 2% peptone, 2% glucose). Crude cell extracts were prepared by disrupting the cells with glass beads or French Press, depending on fermenter sizes. After centrifugation, the cell-free extracts were resuspended in cell breaking buffer (50 mM Tris, pH7.4, 100 mM KCl, 1 mM EDTA) in the presence of a protease inhibitor cocktail, before aliquoting and freezing at −20° C.

CPT activity was measured using a spectrophotometric assay using 5,5'-dithio-bis-(2-nitrobenzoic acid) (DTNB) also called Ellman's reagent. The HS-CoA released on the formation of acylcarnitine from carnitine (500 μM) and palmitoyl-CoA (80 μM) reduced DTNB (300 μM) forming 5-mercapto-2-nitrobenzoic acid which absorbed at 410 nm with a molar extinction coefficient of 13600 $M^{-1}cm^{-1}$. The assay buffer contained 120 mM KCl, 25 mM Tris, pH 7.4, 1 mM EDTA. This assay was used for the identification of CPT inhibitors, particularly/preferentially CPT2-selective inhibitors, versus the liver and muscle CPT1 isoforms.

The compounds according to formula I preferably have an $IC_{50}$ value (CPT2) below 10 μM, preferably 1 nM to 10 μM, more preferably 1 nM to 1 μM. The following table shows data for some examples.

| Example | hCPT2 inhibition IC$_{50}$ [µmol/l] | hL-CPT1 inhibition IC$_{50}$ [µmol/l] |
|---|---|---|
| 1 | 0.910 | 7.77 |
| 2 | 3.492 | >10 |
| 6 | 0.189 | >10 |
| 7 | 0.591 | 5.99 |
| 8 | 0.152 | >10 |
| 9 | 0.002 | 5.79 |
| 10 | 0.694 | >10 |
| 11 | 2.943 | >10 |
| 12 | 0.300 | >10 |
| 13 | 2.634 | >10 |
| 14 | 0.783 | >10 |
| 15 | 2.063 | 6.55 |
| 17 | 1.557 | >10 |
| 18 | 0.452 | >10 |
| 19 | 0.016 | 2.33 |
| 20 | 0.021 | 1.00 |
| 21 | 0.265 | 6.68 |
| 22 | 0.268 | 8.63 |
| 23 | 0.071 | 1.66 |
| 24 | 0.073 | 5.36 |
| 25 | 0.019 | 1.47 |
| 26 | 0.400 | 1.15 |
| 27 | 0.170 | 2.19 |
| 28 | 0.015 | 5.44 |
| 29 | 0.160 | >10 |
| 30 | 0.036 | n.d. |
| 31 | 0.058 | 2.41 |
| 32 | 0.143 | 7.02 |
| 33 | 0.948 | >10 |
| 34 | 0.122 | 4.32 |
| 35 | 0.046 | 3.59 |
| 36 | 0.317 | >10 |
| 37 | 0.241 | >10 |
| 38 | 0.017 | 6.91 |
| 39 | 0.003 | >10 |
| 40 | 0.044 | 6.55 |
| 41 | 0.098 | 7.72 |
| 42 | 0.022 | 2.34 |
| 43 | 0.118 | 7.31 |
| 44 | 1.061 | >10 |
| 50 | 2.103 | >10 |
| 51 | 0.184 | 1.06 |
| 54 | 0.082 | n.d. |
| 55 | 0.065 | n.d. |
| 56 | 0.101 | n.d. |
| 62 | 1.437 | n.d. |
| 63 | 0.332 | 2.87 |

The compounds of formula I and/or their pharmaceutically acceptable salts can be used as medicaments, e.g. in the form of pharmaceutical preparations for enteral, parenteral or topical administration. They can be administered, for example, perorally, e.g. in the form of tablets, coated tablets, dragées, hard and soft gelatine capsules, solutions, emulsions or suspensions, rectally, e.g. in the form of suppositories, parenterally, e.g. in the form of injection solutions or suspensions or infusion solutions, or topically, e.g. in the form of ointments, creams or oils. Oral administration is preferred.

The production of the pharmaceutical preparations can be effected in a manner which will be familiar to any person skilled in the art by bringing the described compounds of formula I and/or their pharmaceutically acceptable salts, optionally in combination with other therapeutically valuable substances, into a galenical administration form together with suitable, non-toxic, inert, therapeutically compatible solid or liquid carrier materials and, if desired, usual pharmaceutical adjuvants.

Suitable carrier materials are not only inorganic carrier materials, but also organic carrier materials. Thus, for example, lactose, corn starch or derivatives thereof, talc, stearic acid or its salts can be used as carrier materials for tablets, coated tablets, dragées and hard gelatine capsules. Suitable carrier materials for soft gelatine capsules are, for example, vegetable oils, waxes, fats and semi-solid and liquid polyols (depending on the nature of the active ingredient no carriers might, however, be required in the case of soft gelatine capsules). Suitable carrier materials for the production of solutions and syrups are, for example, water, polyols, sucrose, invert sugar and the like. Suitable carrier materials for injection solutions are, for example, water, alcohols, polyols, glycerol and vegetable oils. Suitable carrier materials for suppositories are, for example, natural or hardened oils, waxes, fats and semi-liquid or liquid polyols. Suitable carrier materials for topical preparations are glycerides, semi-synthetic and synthetic glycerides, hydrogenated oils, liquid waxes, liquid paraffins, liquid fatty alcohols, sterols, polyethylene glycols and cellulose derivatives.

Usual stabilizers, preservatives, wetting and emulsifying agents, consistency-improving agents, flavor-improving agents, salts for varying the osmotic pressure, buffer substances, solubilizers, colorants and masking agents and antioxidants come into consideration as pharmaceutical adjuvants.

The dosage of the compounds of formula I can vary within wide limits depending on the disease to be controlled, the age and the individual condition of the patient and the mode of administration, and will, of course, be fitted to the individual requirements in each particular case. For adult patients a daily dosage of about 1 to 2000 mg, especially about 1 to 500 mg, comes into consideration. Depending on the severity of the disease and the precise pharmacokinetic profile the compound could be administered with one or several daily dosage units, e.g. in 1 to 3 dosage units.

The pharmaceutical preparations conveniently contain about 1 to 500 mg, preferably 1 to 200 mg, of a compound of formula I.

The following examples serve to illustrate the present invention in more detail. They are, however, not intended to limit its scope in any manner.

EXAMPLES

Abbreviations

HPLC=high pressure liquid chromatography, m/e=mass to charge ratio as measured by mass spectrometry (MS).

Example 1

(R)-3-[8-(3,4-Difluoro-benzyloxy)-octanoylamino]-4-dimethylamino-butyric acid

Step 1: A solution of 1,8-octanediol (300 mg, 2.05 mmol) in tetrahydrofuran/N,N-dimethylformamide 2:1 (3 mL) was added dropwise at 0° C. to a suspension of sodium hydride (60% dispersion in mineral oil, 90 mg, 2.3 mmol) in N,N-dimethylformamide (1.5 mL), then after 2 h 3,4-difluorobenzyl bromide (445 mg, 2.15 mmol) was added. After 4 h the reaction mixture was partitioned between water and ethyl acetate. The organic layer was washed with brine, dried over sodium sulfate, filtered, and evaporated. Chromatography (SiO$_2$, heptane-ethyl acetate gradient) afforded 8-(3,4-difluoro-benzyloxy)-octan-1-ol (258 mg, 46%). Colorless oil, m/e=273.3 ([M+H]$^+$).

Step 2: Pyridinium dichromate (1.23 g, 3.27 mmol) was added at 0° C. to a solution of 8-(3,4-difluoro-benzyloxy)-octan-1-ol (254 mg, 0.93 mmol) in N,N-dimethyl-formamide (2 mL). The reaction mixture was allowed to reach room temperature over 16 h, then partitioned between water and ethyl acetate. The organic layer was washed with brine, dried over sodium sulfate, filtered, and evaporated. Chromatography (SiO$_2$, heptane-[ethyl acetate/formic acid 100:1] gradient) afforded 8-(3,4-difluoro-benzyloxy)-octanoic acid (162 mg, 61%). Colorless oil, m/e=285.1 ([M−H]$^-$).

Step 3: A solution of 8-(3,4-difluoro-benzyloxy)-octanoic acid (153 mg, 0.53 mmol), N,N-diisopropylethylamine (414 mg, 3.21 mmol), and O-(7-azabenzotriazol-1-yl)-N,N,N',N'-tetrametbyluronium-hexaflurophophate (244 mg, 0.64 mmol) in N,N-dimethylformamide was stirred for 1 h at room temperature, then a solution of (R)-3-amino-4-dimethylamino-butyric acid benzyl ester dihydrochloride (198 mg, 0.64 mmol) in N,N-dimethylformamide (1 mL) was added. The reaction mixture was stirred for 16 h at room temperature, then evaporated. Chromatography (SiO$_2$, dichloromethane-[dichloromethane/methanol/25% aq. ammonia solution 110:10:1] gradient) produced (R)-3-[8-(3,4-difluoro-benzyloxy)-octanoylamino]-4-dimethylamino-butyric acid benzyl ester (136 mg, 50%). Light yellow oil, m/e=505.4 ([M+H]$^+$).

Step 4: A solution of (R)-3-[8-(3,4-difluoro-benzyloxy)-octanoylamino]-4-dimethylamino-butyric acid benzyl ester (125 mg, 0.25 mmol) was hydrogenated under atmospheric pressure in the presence of palladium (10% on activated charcoal, 30 mg). After 30 min, the catalyst was filtered off and the filtrate concentrated and dried to afford (R)-3-[8-(3,4-difluoro-benzyloxy)-octanoylamino]-4-dimethylamino-butyric acid (96 mg, 89%). Light yellow oil, m/e=413.2 ([M−H]$^-$).
Preparation of (R)-3-amino-4-dimethylamino-butyric acid benzyl ester dihydrochloride a) Triethylamine (2.8 mL, 20.0 mmol) was added at 0° C. to a solution of Boc-D-aspartic acid 4-benzyl ester (5.00 g, 15.0 mmol) in dichloromethane, then ethyl chloroformate (1.91 mL, 20.0 mmol) was added dropwise. The reaction mixture was stirred for 1 h at 0° C., then a solution of dimethylamine hydrochloride (2.65 g, 32.0 mmol) and triethylamine (4.53 mL, 32.0 mmol) in dichloromethane (100 mL) were added dropwise. The reaction mixture was allowed to reach room temperature over 16 h, then washed with brine, and concentrated. Chromatography (SiO$_2$; heptane-ethyl acetate gradient) produced (R)-3-tert-butoxycarbonylamino-N,N-dimethyl-succinamic acid benzyl ester (3.77 g, 70%). Colorless oil, m/e=351.4 ([M+H]$^+$).

b) Borane-dimethyl sulfide complex (1.57 mL, 3.14 mmol) was added dropwise at 0° C. to a solution of (R)-3-tert-butoxycarbonylamino-N,N-dimethyl-succinamic acid benzyl ester (500 mg, 1.43 mmol). The reaction mixture was warmed to room temperature and heated at reflux for 3 hours, then cooled to 0° C. and treated dropwise with 6 M aq. hydrochloric acid solution (0.68 mL, 4.1 mmol). The reaction mixture was allowed to warm to room temperature and concentrated in vacuo. Residual water was azeotroped with toluene and concentrated under high vacuum to afford (R)-3-amino-4-dimethylamino-butyric acid benzyl ester dihydrochloride (384 mg, 87%). White solid, m/e=237.4 ([M+H]$^+$).

Example 2

(R)-3-[8-(2,5-Difluoro-benzyloxy)-octanoylamino]-4-dimethylamino-butyric acid

The title compound, m/e=413.3 ([M−H]$^-$), was produced in analogy with example 1, steps 1 to 4. Thus, 1,8-octanediol was alkylated in step 1 with 2,5-difluorobenzyl bromide, leading to 8-(2,5-difluoro-benzyloxy)-octan-1-ol, which was oxidized in step 2 to 8-(2,5-difluoro-benzyloxy)-octanoic acid. This was coupled in step 3 with (R)-3-amino-4-dimethylamino-butyric acid benzyl ester dihydrochloride to produce (R)-3-[8-(2,5-difluoro-benzyloxy)-octanoylamino]-4-dimethylamino-butyric acid benzyl ester, which was hydrogenated in step 4.

Example 3

(R)-3-[8-(2,4-Difluoro-benzyloxy)-octanoylamino]-4-dimethylamino-butyric acid

The title compound, m/e=413.1 ([M−H]$^-$), was produced in analogy with example 1, steps 1 to 4. Thus, 1,8-octanediol was alkylated in step 1 with 2,4-difluorobenzyl bromide, leading to 8-(2,4-difluoro-benzyloxy)-octan-1-ol, which was oxidized in step 2 to 8-(2,4-difluoro-benzyloxy)-octanoic acid. This was coupled in step 3 with (R)-3-amino-4-dimethylamino-butyric acid benzyl ester dihydrochloride to produce (R)-3-[8-(2,4-difluoro-benzyloxy)-octanoylamino]-4-dimethylamino-butyric acid benzyl ester, which was hydrogenated in step 4.

Example 4

(R)-4-Dimethylamino-3-[8-(2,3,4-trifluoro-benzyloxy)-octanoylamino]-butyric acid The title compound, m/e=432.5 ([M+H]$^+$), was produced in analogy with example 1, steps 1 to 4. Thus, 1,8-octanediol was alkylated in step 1 with 2,3,4-trifluorobenzyl bromide, leading to 8-(2,3,4-trifluoro-benzyloxy)-octan-1-ol, which was oxidized in step 2 to 8-(2,3,4-trifluoro-benzyloxy)-octanoic acid. This was coupled in step 3 with (R)-3-amino-4-dimethylamino-butyric acid benzyl ester dihydrochloride to produce (R)-3-[8-(2,3,4-trifluoro-benzyloxy)-octanoylamino]-4-dimethylamino-butyric acid benzyl ester, which was hydrogenated in step 4.

Example 5

(R)-4-Dimethylamino-3-(8-pentafluorophenyl-methoxy-octanoylamino)-butyric acid

The title compound, m/e=467.5 ([M−H]$^-$), was produced in analogy with example 1, steps 1 to 4. Thus, 1,8-octanediol was alkylated in step 1 with pentafluorobenzyl bromide, leading to 8-(pentafluoro-benzyloxy)-octan-1-ol, which was oxidized in step 2 to 8-(pentafluoro-benzyloxy)-octanoic acid. This was coupled in step 3 with (R)-3-amino-4-dimethylamino-butyric acid benzyl ester dihydrochloride to produce (R)-3-[8-(pentafluoro-benzyloxy)-octanoylamino]-4-dimethylamino-butyric acid benzyl ester, which was hydrogenated in step 4.

Example 6

(R)-4-Dimethylamino-3-[8-(4-trifluoromethyl-benzyloxy)-octanoylamino]-butyric acid The title compound, m/e=445.6 ([M−H]$^-$), was produced in analogy with example 1, steps 1 to 4. Thus, 1,8-octanediol was alkylated in step 1 with 4-trifluoromethyl-benzyl bromide, leading to 8-(4-trifluoromethyl-benzyloxy)-octan-1-ol, which was oxidized in step 2 to 8-(4-trifluoromethyl-benzyloxy)-octanoic acid. This was coupled in step 3 with (R)-3-amino-4-dimethylamino-butyric acid benzyl ester dihydrochloride to produce (R)-3-[8-(4-trifluoromethyl-benzyloxy)-octanoylamino]-4-dimethylamino-butyric acid benzyl ester, which was hydrogenated in step 4.

Example 7

(R)-4-Dimethylamino-3-[8-(3-fluoro-4-trifluoromethyl-benzyloxy)-octanoylamino]-butyric acid The title compound, m/e=463.5 ([M−H]⁻), was produced in analogy with example 1, steps 1 to 4. Thus, 1,8-octanediol was alkylated in step 1 with 3-fluoro-4-trifluoromethyl-benzyl bromide, leading to 8-(3-fluoro-4-trifluoromethyl-benzyloxy)-octan-1-ol, which was oxidized in step 2 to 8-(3-fluoro-4-trifluoromethyl-benzyloxy)-octanoic acid. This was coupled in step 3 with (R)-3-amino-4-dimethylamino-butyric acid benzyl ester dihydrochloride to produce (R)-3-[8-(3-fluoro-4-trifluoromethyl-benzyloxy)-octanoylamino]-4-dimethylamino-butyric acid benzyl ester, which was hydrogenated in step 4.

Example 8

(R)-4-Dimethylamino-3-[8-(4-methoxy-benzyloxy)-octanoylamino]-butyric acid

The title compound, m/e=407.6 ([M−H]⁻), was produced in analogy with example 1, steps 1 to 4. Thus, 1,8-octanediol was alkylated in step 1 with 4-methoxy-benzyl bromide, leading to 8-(4-methoxy-benzyloxy)-octan-1-ol, which was oxidized in step 2 to 8-(4-methoxy-benzyloxy)-octanoic acid. This was coupled in step 3 with (R)-3-amino-4-dimethylamino-butyric acid benzyl ester dihydrochloride to produce (R)-3-[8-(4-methoxy-benzyloxy)-octanoylamino]-4-dimethylamino-butyric acid benzyl ester, which was hydrogenated in step 4.

Example 9

(R)-3-[8-(Biphenyl-4-ylmethoxy)-octanoylamino]-4-dimethylamino-butyric acid

The title compound, m/e=455.3 ([M+H]⁺), was produced in analogy with example 1, steps 1 to 4. Thus, 1,8-octanediol was alkylated in step 1 with 4-(bromomethyl)-biphenyl, leading to 8-(biphenyl-4-ylmethoxy)-octan-1-ol, which was oxidized in step 2 to 8-(biphenyl-4-ylmethoxy)-octanoic acid. This was coupled in step 3 with (R)-3-amino-4-dimethylamino-butyric acid benzyl ester dihydrochloride to produce (R)-3-[8-(biphenyl-4-ylmethoxy)-octanoylamino]-4-dimethylamino-butyric acid benzyl ester, which was hydrogenated in step 4.

Example 10

(R)-4-Dimethylamino-3-[8-(2-fluoro-4-trifluoromethyl-benzyloxy)-octanoylamino]-butyric acid The title compound, m/e=463.1 ([M−H]⁻), was produced in analogy with example 1, steps 1 to 4. Thus, 1,8-octanediol was alkylated in step 1 with 2-fluoro-4-trifluoromethyl-benzyl bromide, leading to 8-(2-fluoro-4-trifluoromethyl-benzyloxy)-octan-1-ol, which was oxidized in step 2 to 8-(2-fluoro-4-trifluoromethyl-benzyloxy)-octanoic acid. This was coupled in step 3 with (R)-3-amino-4-dimethylamino-butyric acid benzyl ester dihydrochloride to produce (R)-3-[8-(2-fluoro-4-trifluoromethyl-benzyloxy)-octanoylamino]-4-dimethylamino-butyric acid benzyl ester, which was hydrogenated in step 4.

Example 11

(R)-4-Dimethylamino-3-[8-(2,3,5,6-tetrafluoro-4-methoxy-benzyloxy)-octanoylamino]-butyric acid The title compound, m/e=479.4 ([M−H]⁻), was produced in analogy with example 1, steps 1 to 4. Thus, 1,8-octanediol was alkylated in step 1 with 2,3,5,6-tetrafluoro-4-methoxy-benzyl bromide, leading to 8-(2,3,5,6-tetrafluoro-4-methoxy-benzyloxy)-octan-1-ol, which was oxidized in step 2 to 8-(2,3,5,6-tetrafluoro-4-methoxy-benzyloxy)-octanoic acid. This was coupled in step 3 with (R)-3-amino-4-dimethylamino-butyric acid benzyl ester dihydrochloride to produce (R)-3-[8-(2,3,5,6-tetrafluoro-4-methoxy-benzyloxy)-octanoylamino]-4-dimethylamino-butyric acid benzyl ester, which was hydrogenated in step 4.

Example 12

(R)-4-Dimethylamino-3-[8-(naphthalen-1-ylmethoxy)-octanoylamino]-butyric acid

The title compound, m/e=427.1 ([M−H]⁻), was produced in analogy with example 1, steps 1 to 4. Thus, 1,8-octanediol was alkylated in step 1 with 1-bromomethyl-naphthalene, leading to 8-(naphthalen-1-ylmethoxy)-octan-1-ol, which was oxidized in step 2 to 8-(naphthalen-1-ylmethoxy)-octanoic acid. This was coupled in step 3 with (R)-3-amino-4-dimethylamino-butyric acid benzyl ester dihydrochloride to produce (R)-3-[8-(naphthalen-1-ylmethoxy)-octanoylamino]-4-dimethylamino-butyric acid benzyl ester, which was hydrogenated in step 4.

Example 13

(R)-4-Dimethylamino-3-[8-(2-fluoro-benzyloxy)-octanoylamino]-butyric acid

The title compound, m/e=397.4 ([M+H]⁺), was produced in analogy with example 1, steps 1 to 4. Thus, 1,8-octanediol was alkylated in step 1 with 2-fluorobenzyl bromide, leading to 8-(2-fluoro-benzyloxy)-octan-1-ol, which was oxidized in step 2 to 8-(2-fluoro-benzyloxy)-octanoic acid. This was coupled in step 3 with (R)-3-amino-4-dimethylamino-butyric acid benzyl ester dihydrochloride to produce (R)-3-[8-(2-fluoro-benzyloxy)-octanoylamino]-4-dimethylamino-butyric acid benzyl ester, which was hydrogenated in step 4.

Example 14

(R)-4-Dimethylamino-3-[8-(3-fluoro-benzyloxy)-octanoylamino]-butyric acid

The title compound, m/e=397.4 ([M−H]⁺), was produced in analogy with example 1, steps 1 to 4. Thus, 1,8-octanediol was alkylated in step 1 with 3-fluorobenzyl bromide, leading to 8-(3-fluoro-benzyloxy)-octan-1-ol, which was oxidized in step 2 to 8-(3-fluoro-benzyloxy)-octanoic acid. This was coupled in step 3 with (R)-3-amino-4-dimethylamino-butyric acid benzyl ester dihydrochloride to produce (R)-3-[8-(3-fluoro-benzyloxy)-octanoylamino]-4-dimethylamino-butyric acid benzyl ester, which was hydrogenated in step 4.

Example 15

(R)-4-Dimethylamino-3-[8-(4-fluoro-benzyloxy)-octanoylamino]-butyric acid

The title compound, m/e=397.4 ([M+H]$^+$), was produced in analogy with example 1, steps 1-4. Thus, 1,8-octanediol was alkylated in step 1 with 4-fluorobenzyl bromide, leading to 8-(4-fluoro-benzyloxy)-octan-1-ol, which was oxidized in step 2 to 8-(4-fluoro-benzyloxy)-octanoic acid. This was coupled in step 3 with (R)-3-amino-4-dimethylamino-butyric acid benzyl ester dihydrochloride to produce (R)-3-[8-(4-fluoro-benzyloxy)-octanoylamino]-4-dimethylamino-butyric acid benzyl ester, which was hydrogenated in step 4.

Example 16

(R)-3-[8-(2,3-Difluoro-benzyloxy)-octanoylamino]-4-dimethylamino-butyric acid

The title compound, m/e=415.5 ([M+H]$^+$), was produced in analogy with example 1, steps 1-4. Thus, 1,8-octanediol was alkylated in step 1 with 2,3-difluorobenzyl bromide, leading to 8-(2,3-difluoro-benzyloxy)-octan-1-ol, which was oxidized in step 2 to 8-(2,3-difluoro-benzyloxy)-octanoic acid. This was coupled in step 3 with (R)-3-amino-4-dimethylamino-butyric acid benzyl ester dihydrochloride to produce (R)-3-[8-(2,3-difluoro-benzyloxy)-octanoylamino]-4-dimethylamino-butyric acid benzyl ester, which was hydrogenated in step 4.

Example 17

(R)-3-(8-Benzyloxy-octanoylamino)-4-dimethylamino-butyric acid

The title compound, m/e=377.6 ([M−H]$^-$), was produced in analogy with example 1, steps 1 to 4. Thus, 1,8-octanediol was alkylated in step 1 with benzyl bromide, leading to 8-benzyloxy-octan-1-ol, which was oxidized in step 2 to 8-benzyloxy-octanoic acid. This was coupled in step 3 with (R)-3-amino-4-dimethylamino-butyric acid benzyl ester dihydrochloride to produce (R)-3-[8-benzyloxy)-octanoylamino]-4-dimethylamino-butyric acid benzyl ester, which was hydrogenated in step 4.

Example 18

(R)-4-Dimethylamino-3-[9-(2-fluoro-phenoxy)-nonanoylamino]-butyric acid

Step 1: Potassium carbonate (2.59 g, 18.7 mmol) and 9-bromo-1-nonanol (1.39 g, 6.24 mmol) were added at room temperature to a solution of 2-fluorophenol (700 mg, 6.24 mmol) in N,N-dimethylformamide (20 mL), then after 40 h insoluble material was removed by filtration. The filtrate was evaporated and the residue taken up in dichloromethane, washed with 1 M aq. sodium hydroxide solution, dried over sodium sulfate, filtered, and evaporated, to afford 9-(2-fluoro-phenoxy)-nonan-1-ol (1.7 g), which was directly used in the next step.

Step 2: Oxidation of 9-(2-fluoro-phenoxy)-nonan-1-ol in analogy with example 1, step 2 gave 9-(2-fluoro-phenoxy)-nonanoic acid.

Step 3: Amide coupling of 9-(2-fluoro-phenoxy)-nonanoic acid with (R)-3-amino-4-dimethylamino-butyric acid benzyl ester dihydrochloride in analogy with example 1, step 3 led to (R)-4-dimethylamino-3-[9-(2-fluoro-phenoxy)-nonanoylamino]-butyric acid benzyl ester.

Step 4: Hydrogenation of (R)-4-dimethylamino-3-[9-(2-fluoro-phenoxy)-nonanoylamino]-butyric acid benzyl ester in analogy with example 1, step 4 produced (R)-4-dimethylamino-3-[9-(2-fluoro-phenoxy)-nonanoylamino]-butyric acid. White solid, m/e=395.5 ([M−H]$^-$).

Example 19

(R)-4-Dimethylamino-3-[9-(3-fluoro-phenoxy)-nonanoylamino]-butyric acid

The title compound, m/e=397.4 ([M+H]$^+$), was produced in analogy with example 18, steps 1 to 4. Thus, 3-fluorophenol was alkylated in step 1 with 9-bromo-1-nonanol, leading to 9-(3-fluoro-phenoxy)-nonan-1-ol, which was oxidized in step 2 to 9-(3-fluoro-phenoxy)-nonanoic acid. This was coupled in step 3 with (R)-3-amino-4-dimethylamino-butyric acid benzyl ester dihydrochloride to produce (R)-4-dimethylamino-3-[9-(3-fluoro-phenoxy)-nonanoylamino]-butyric acid benzyl ester, which was hydrogenated in step 4.

Example 20

(R)-4-Dimethylamino-3-[9-(4-fluoro-phenoxy)-nonanoylamino]-butyric acid

The title compound, m/e=395.5 ([M−H]$^-$), was produced in analogy with example 18, steps 1 to 4. Thus, 4-fluorophenol was alkylated in step 1 with 9-bromo-1-nonanol, leading to 9-(4-fluoro-phenoxy)-nonan-1-ol, which was oxidized in step 2 to 9-(4-fluoro-phenoxy)-nonanoic acid. This was coupled in step 3 with (R)-3-amino-4-dimethylamino-butyric acid benzyl ester dihydrochloride to produce (R)-4-dimethylamino-3-[9-(4-fluoro-phenoxy)-nonanoylamino]-butyric acid benzyl ester, which was hydrogenated in step 4.

Example 21

(R)-3-[9-(2,3-Difluoro-phenoxy)-nonanoylamino]-4-dimethylamino-butyric acid

The title compound, m/e=415.5 ([M+H]$^+$), was produced in analogy with example 18, steps 1 to 4. Thus, 2,3-difluorophenol was alkylated in step 1 with 9-bromo-1-nonanol, leading to 9-(2,3-difluoro-phenoxy)-nonan-1-ol, which was oxidized in step 2 to 9-(2,3-difluoro-phenoxy)-nonanoic acid. This was coupled in step 3 with (R)-3-amino-4-dimethylamino-butyric acid benzyl ester dihydrochloride to produce (R)-4-dimethylamino-3-[9-(2,3-difluoro-phenoxy)-nonanoylamino]-butyric acid benzyl ester, which was hydrogenated in step 4.

Example 22

(R)-3-[9-(2,4-Difluoro-phenoxy)-nonanoylamino]-4-dimethylamino-butyric acid

The title compound, m/e=413.6 ([M−H]$^-$), was produced in analogy with example 18, steps 1 to 4. Thus, 2,4-difluorophenol was alkylated in step 1 with 9-bromo-1-nonanol, leading to 9-(2,4-difluoro-phenoxy)-nonan-1-ol, which was oxidized in step 2 to 9-(2,4-difluoro-phenoxy)-nonanoic acid. This was coupled in step 3 with (R)-3-amino-4-dimethylamino-butyric acid benzyl ester dihydrochloride to produce (R)-4-dimethylamino-3-[9-(2,4-difluoro-phenoxy)-nonanoylamino]-butyric acid benzyl ester, which was hydrogenated in step 4.

Example 23

(R)-3-[9-(3,4-Difluoro-phenoxy)-nonanoylamino]-4-dimethylamino-butyric acid

The title compound, m/e=413.6 ([M−H]$^-$), was produced in analogy with example 18, steps 1 to 4. Thus, 3,4-difluorophenol was alkylated in step 1 with 9-bromo-1-nonanol, leading to 9-(3,4-difluoro-phenoxy)-nonan-1-ol, which was oxidized in step 2 to 9-(3,4-difluoro-phenoxy)-nonanoic acid. This was coupled in step 3 with (R)-3-amino-4-dimethylamino-butyric acid benzyl ester dihydrochloride to produce (R)-4-dimethylamino-3-[9-(3,4-difluoro-phenoxy)-nonanoylamino]-butyric acid benzyl ester, which was hydrogenated in step 4.

Example 24

(R)-4-Dimethylamino-3-[9-(2,3,4-trifluoro-phenoxy)-nonanoylamino]-butyric acid

The title compound, m/e=433.5 ([M+H]$^+$), was produced in analogy with example 18, steps 1 to 4. Thus, 2,3,4-trifluorophenol was alkylated in step 1 with 9-bromo-1-nonanol, leading to 9-(2,3,4-trifluoro-phenoxy)-nonan-1-ol, which was oxidized in step 2 to 9-(2,3,4-trifluoro-phenoxy)-nonanoic acid. This was coupled in step 3 with (R)-3-amino-4-dimethylamino-butyric acid benzyl ester dihydrochloride to produce (R)-4-dimethylamino-3-[9-(2,3,4-trifluoro-phenoxy)-nonanoylamino]-butyric acid benzyl ester, which was hydrogenated in step 4.

Example 25

(R)-3-[9-(Biphenyl-4-yloxy)-nonanoylamino]-4-dimethylamino-butyric acid

The title compound, m/e=455.3 ([M+H]$^+$), was produced in analogy with example 18, steps 1 to 4. Thus, biphenyl-4-ol was alkylated in step 1 with 9-bromo-1-nonanol, leading to 9-(biphenyl-4-yloxy)-nonan-1-ol, which was oxidized in step 2 to 9-(biphenyl-4-yloxy)-nonanoic acid. This was coupled in step 3 with (R)-3-amino-4-dimethylamino-butyric acid benzyl ester dihydrochloride to produce (R)-4-dimethylamino-3-[9-(biphenyl-4-yloxy)-nonanoylamino]-butyric acid benzyl ester, which was hydrogenated in step 4.

Example 26

(R)-3-[9-(3,4-Dimethoxy-phenoxy)-nonanoylamino]-4-dimethylamino-butyric acid

The title compound, m/e=439.4 ([M+H]$^+$), was produced in analogy with example 18, steps 1 to 4. Thus, 3,4-dimethoxyphenol was alkylated in step 1 with 9-bromo-1-nonanol, leading to 9-(3,4-dimethoxy-phenoxy)-nonan-1-ol, which was oxidized in step 2 to 9-(3,4-dimethoxy-phenoxy)-nonanoic acid. This was coupled in step 3 with (R)-3-amino-4-dimethylamino-butyric acid benzyl ester dihydrochloride to produce (R)-4-dimethylamino-3-[9-(3,4-dimethoxy-phenoxy)-nonanoylamino]-butyric acid benzyl ester, which was hydrogenated in step 4.

Example 27

(R)-4-Dimethylamino-3-[9-(4-trifluoromethyl-phenoxy)-nonanoylamino]-butyric acid The title compound, m/e=447.4 ([M+H]$^+$), was produced in analogy with example 18, steps 1 to 4. Thus, 4-trifluoromethyl-phenol was alkylated in step 1 with 9-bromo-1-nonanol, leading to 9-(4-trifluoromethyl-phenoxy)-nonan-1-ol, which was oxidized in step 2 to 9-(4-trifluoromethyl-phenoxy)-nonanoic acid. This was coupled in step 3 with (R)-3-amino-4-dimethylamino-butyric acid benzyl ester dihydrochloride to produce (R)-4-dimethylamino-3-[9-(4-trifluoromethyl-phenoxy)-nonanoylamino]-butyric acid benzyl ester, which was hydrogenated in step 4.

Example 28

(R)-4-Dimethylamino-3-[9-(4-methoxy-phenoxy)-nonanoylamino]-butyric acid

The title compound, m/e=409.5 ([M+H]$^+$), was produced in analogy with example 18, steps 1 to 4. Thus, 4-methoxyphenol was alkylated in step 1 with 9-bromo-1-nonanol, leading to 9-(4-methoxy-phenoxy)-nonan-1-ol, which was oxidized in step 2 to 9-(4-methoxy-phenoxy)-nonanoic acid. This was coupled in step 3 with (R)-3-amino-4-dimethylamino-butyric acid benzyl ester dihydrochloride to produce (R)-4-dimethylamino-3-[9-(4-methoxy-phenoxy)-nonanoylamino]-butyric acid benzyl ester, which was hydrogenated in step 4.

Example 29

(R)-4-Dimethylamino-3-[9-(naphthalen-1-yloxy)-nonanoylamino]-butyric acid

The title compound, m/e=429.5 ([M+H]$^+$), was produced in analogy with example 18, steps 1 to 4. Thus, naphthalen-1-ol was alkylated in step 1 with 9-bromo-1-nonanol, leading to 9-(naphthalen-1-yloxy)-nonan-1-ol, which was oxidized in step 2 to 9-(naphthalen-1-yloxy)-nonanoic acid. This was coupled in step 3 with (R)-3-amino-4-dimethylamino-butyric acid benzyl ester dihydrochloride to produce (R)-4-dimethylamino-3-[9-(naphthalen-1-yloxy)-nonanoylamino]-butyric acid benzyl ester, which was hydrogenated in step 4.

Example 30

(R)-4-Dimethylamino-3-(11-phenoxy-undecanoylamino)-butyric acid

The title compound, m/e=405.7 ([M−H]$^-$), was produced in analogy with example 18, steps 1 to 4. Thus, phenol was alkylated in step 1 with 11-bromo-1-undecanol, leading to 11-phenoxy-undecan-1-ol, which was oxidized in step 2 to 11-phenoxy-undecanoic acid. This was coupled in step 3 with (R)-3-amino-4-dimethylamino-butyric acid benzyl ester dihydrochloride to produce (R)-4-dimethylamino-3-[11-phenoxy-undecanoylamino]-butyric acid benzyl ester, which was hydrogenated in step 4.

Example 31

(R)-4-Dimethylamino-3-(9-phenoxy-nonanoylamino)-butyric acid

The title compound, m/e=379.4 ([M+H]$^+$), was produced in analogy with example 18, steps 1 to 4. Thus, phenol was alkylated in step 1 with 9-bromo-1-nonanol, leading to 9-phenoxy-nonan-1-ol, which was oxidized in step 2 to 9-phenoxy-nonanoic acid. This was coupled in step 3 with (R)-3-amino-4-dimethylamino-butyric acid benzyl ester dihydrochloride to produce (R)-4-dimethylamino-3-[9-phenoxy-nonanoylamino]-butyric acid benzyl ester, which was hydrogenated in step 4.

Example 32

(R)-4-Dimethylamino-3-(10-phenyl-decanoylamino)-butyric acid

The title compound, m/e=377.3 ([M+H]$^+$), was produced in analogy with example 1, steps 3 and 4. Thus, commercially available 10-phenyldecanoic acid was coupled in step 3 with (R)-3-amino-4-dimethylamino-butyric acid benzyl ester dihydrochloride to produce (R)-4-dimethylamino-3-(10-phenyl-decanoylamino)-butyric acid benzyl ester, which was hydrogenated in step 4.

Example 33

(S)-4-Dimethylamino-3-(10-phenyl-decanoylamino)-butyric acid

The title compound, m/e=377.5 ([M+H]$^+$), was produced in analogy with example 1, steps 3 and 4. Thus, commercially available 10-phenyldecanoic acid was coupled in step 3 with (S)-3-amino-4-dimethylamino-butyric acid benzyl ester dihydrochloride to produce (S)-4-dimethylamino-3-(10-phenyl-decanoylamino)-butyric acid benzyl ester, which was hydrogenated in step 4.

(S)-3-Amino-4-dimethylamino-butyric acid benzyl ester dihydrochloride was prepared in analogy with (R)-3-amino-4-dimethylamino-butyric acid benzyl ester dihydrochloride (example 1), starting from Boc-L-aspartic acid 4-benzyl ester.

Example 34

(R)-4-Dimethylamino-3-[10-(4-fluoro-phenyl)-decanoylamino]-butyric acid

Step 1: To a solution of 9-bromo-nonanoic acid (7.00 g, 29.5 mmol) in toluene (10 mL) was added triphenylphosphine (7.74 g, 29.5 mmol). The solution was sealed under nitrogen in a pressure tube and heated at 110° C. for 18 hours. On reaction completion two phases were observed. The toluene top layer was decanted from the crude product which was washed with toluene. (8-Carboxy-octyl)-triphenyl-phosphonium bromide (14.9 g) was obtained, which was directly used in the next step. White semisolid, m/e=419.3 ([M+H]$^+$).

Step 2: Sodium hydride (60% dispersion in mineral oil; 0.65 g, 16 mmol) was added portionwise at room temperature to a stirred solution of (8-carboxy-octyl)-triphenyl-phosphonium bromide (2.8 g, 5.6 mmol) in tetrahydrofuran (30 mL) at room temperature, then after 1 hour 4-fluorobenzaldehyde (700 mg, 5.64 mmol) was added portionwise to the reaction mixture and the solution stirred for 2 days at room temperature. On reaction completion, water (10 ml) was added and the solution acidified to pH 3 with concentrated hydrochloric acid. The product was extracted with ethyl acetate, the organic layer dried over magnesium sulfate, filtered and evaporated. Chromatography (SiO$_2$, heptane-ethyl acetate 4:1) afforded 10-(4-fluoro-phenyl)-dec-9-enoic acid (280 mg, 19%) as a colorless oil.

Step 3: A solution of 10-(4-fluoro-phenyl)-dec-9-enoic acid (230 mg, 0.87 mmol), oxalyl chloride (0.11 mL, 1.3 mmol), and N,N-dimethylformamide (one drop) in dichloromethane (3 mL) was stirred at room temperature for 2 hours, then volatile material was removed by distillation to afford 10-(4-fluoro-phenyl)-dec-9-enoyl chloride. This was redissolved in dichloromethane, then N,N-diisopropylethylamine (140 mg, 1.04 mmol) was added dropwise, followed by (R)-3-amino-4-dimethylamino-butyric acid benzyl ester dihydrochloride. The reaction mixture was stirred at room temperature for 16 h, then washed with water. The organic layer was evaporated and the residue purified by preparative HPLC to afford (R)-4-dimethylamino-3-[10-(4-fluoro-phenyl)-dec-9-enoylamino]-butyric acid benzyl ester (100 mg, 24%), m/e=483.4 ([M+H]$^+$).

Step 4: Hydrogenation of (R)-4-dimethylamino-3-[10-(4-fluoro-phenyl)-dec-9-enoylamino]-butyric acid benzyl ester in analogy with example 1, step 4 produced (R)-4-dimethylamino-3-[10-(4-fluoro-phenyl)-decanoylamino]-butyric acid, m/e=395.2 ([M+H]$^+$).

Example 35

(R)-4-Dimethylamino-3-[10-(2-fluoro-phenyl)-decanoylamino]-butyric acid

Step 1: To a solution of 9-decenoic acid ethyl ester (*Tetrahedron* 2003, 59, 7973; 500 mg, 2.53 mmol) and 2-fluorostyrene (617 mg, 5.05 mmol) in dichloromethane (12.5 mL) was added dichloro(1,3-dimesityl-4,5-dihydroimidazol-2-ylidene)(phenylmethylene) (tricyclohexylphosphine)ruthenium (107 mg, 0.13 mmol). The mixture was flushed with nitrogen and sealed in a pressure tube, then heated at 40° C. for 18 h. After cooling and evaporation of the solvent, the product was purified by chromatography (SiO$_2$, heptane-dichloromethane 3:1), to afford 10-(2-fluoro-phenyl)-dec-9-enoic acid ethyl ester (420 mg, 57%).

Step 2: To a solution of 10-(2-fluoro-phenyl)-dec-9-enoic acid ethyl ester (420 mg, 1.44 mmol) in tetrahydrofuran (2 mL) was added 2 M aq. lithium hydroxide solution (2 mL, 4 mmol). The reaction mixture was stirred at room temperature for 16 h, then partitioned between 1 M aq. hydrochloric acid solution and ethyl acetate. The organic layer was dried over magnesium sulfate, filtered, and evaporated, to afford 10-(2-fluoro-phenyl)-dec-9-enoic acid (250 mg, 66%).

Step 3: In analogy with example 34, step 3, 10-(2-fluoro-phenyl)-dec-9-enoic acid was converted to 10-(2-fluoro-phenyl)-dec-9-enoyl chloride, then reacted with (R)-3-amino-4-dimethylamino-butyric acid benzyl ester dihydrochloride, leading to (R)-4-dimethylamino-3-[10-(2-fluoro-phenyl)-dec-9-enoylamino]-butyric acid benzyl ester.

Step 4: Hydrogenation of (R)-4-dimethylamino-3-[10-(2-fluoro-phenyl)-dec-9-enoylamino]-butyric acid benzyl ester in analogy with example 1, step 4 produced (R)-4-dimethylamino-3-[10-(2-fluoro-phenyl)-decanoylamino]-butyric acid, m/e=395.2 ([M+H]$^+$).

Example 36

(R)-4-Dimethylamino-3-[10-(2,5-dimethyl-phenyl)-decanoylamino]-butyric acid

The title compound, m/e=405.4 ([M+H]$^+$), was produced in analogy with example 35, steps 1 to 4. Thus, 9-decenoic acid ethyl ester was reacted in step 1 with 2,5-dimethylstyrene, leading to 10-(2,5-dimethyl-phenyl)-dec-9-enoic acid ethyl ester, which was hydrolyzed in step 2 to 10-(2,5-dimethyl-phenyl)-dec-9-enoic acid. In step 3, this was converted to 10-(2,5-dimethyl-phenyl)-dec-9-enoyl chloride, then reacted with (R)-3-amino-4-dimethylamino-butyric acid benzyl ester dihydrochloride, leading to (R)-4-dimethylamino-3-[10-(2,5-dimethyl-phenyl)-dec-9-enoylamino]-butyric acid benzyl ester, which was hydrogenated in step 4.

Example 37

(R)-4-Dimethylamino-3-[10-(2,6-dimethyl-phenyl)-decanoylamino]-butyric acid

The title compound, m/e=405.3 ([M+H]$^+$), was produced in analogy with example 34, steps 2 to 4. Thus 2,6-dimethyl-benzaldehyde was reacted in step 2 with (8-carboxy-octyl)-triphenyl-phosphonium bromide, leading to 10-(2,6-dimethyl-phenyl)-dec-9-enoic acid. In step 3, this was converted to 10-(2,6-dimethyl-phenyl)-dec-9-enoyl chloride, then reacted with (R)-3-amino-4-dimethylamino-butyric acid benzyl ester dihydrochloride, leading to (R)-4-dimethylamino-3-[10-(2,6-dimethyl-phenyl)-dec-9-enoylamino]-butyric acid benzyl ester, which was hydrogenated in step 4.

Example 38

(R)-4-Dimethylamino-3-[10-(4-methoxy-phenyl)-decanoylamino]-butyric acid

The title compound, m/e=407.3 ([M+H]$^+$), was produced in analogy with example 35, steps 1 to 4. Thus, 9-decenoic acid ethyl ester was reacted in step 1 with 4-methoxystyrene, leading to 10-(4-methoxy-phenyl)-dec-9-enoic acid ethyl ester, which was hydrolyzed in step 2 to 10-(4-methoxy-phenyl)-dec-9-enoic acid. In step 3, this was converted to 10-(4-methoxy-phenyl)-dec-9-enoyl chloride, then reacted with (R)-3-amino-4-dimethylamino-butyric acid benzyl ester dihydrochloride, leading to (R)-4-dimethylamino-3-[10-(4-methoxy-phenyl)-dec-9-enoylamino]-butyric acid benzyl ester, which was hydrogenated in step 4.

Example 39

(R)-4-Dimethylamino-3-(10-naphthalen-1-yl-decanoylamino)-butyric acid

The title compound, m/e=427.4 ([M+H]$^+$), was produced in analogy with example 35, steps 1 to 4. Thus, 9-decenoic acid ethyl ester was reacted in step 1 with 1-vinylnaphthalene, leading to 10-(naphthalene-1-yl)-dec-9-enoic acid ethyl ester, which was hydrolyzed in step 2 to 10-(naphthalene-1-yl)-dec-9-enoic acid. In step 3, this was converted to 10-(naphthalene-1-yl-dec-9-enoyl chloride, then reacted with (R)-3-amino-4-dimethylamino-butyric acid benzyl ester dihydrochloride, leading to (R)-4-dimethylamino-3-[10-(naphthalene-1-yl)-dec-9-enoylamino]-butyric acid benzyl ester, which was hydrogenated in step 4.

Example 40

(R)-4-Dimethylamino-3-[10-(4-trifluoromethyl-phenyl)-decanoylamino]-butyric acid The title compound, m/e=445.1 ([M+H]$^+$), was produced in analogy with example 35, steps 1 to 4. Thus, 9-decenoic acid ethyl ester was reacted in step 1 with 4-trifluoromethyl-styrene, leading to 10-(4-trifluoromethyl-phenyl)-dec-9-enoic acid ethyl ester, which was hydrolyzed in step 2 to 10-(4-trifluoromethyl-phenyl)-dec-9-enoic acid. In step 3, this was converted to 10-(4-trifluoromethyl-phenyl)-dec-9-enoyl chloride, then reacted with (R)-3-amino-4-dimethylamino-butyric acid benzyl ester dihydrochloride, leading to (R)-4-dimethylamino-3-[10-(4-trifluoromethyl-phenyl)-dec-9-enoylamino]-butyric acid benzyl ester, which was hydrogenated in step 4.

Example 41

(R)-4-Dimethylamino-3-[10-(3-fluoro-phenyl)-decanoylamino]-butyric acid

The title compound, m/e=395.3 ([M+H]$^+$), was produced in analogy with example 35, steps 1 to 4. Thus, 9-decenoic acid ethyl ester was reacted in step 1 with 3-fluorostyrene, leading to 10-(3-fluoro-phenyl)-dec-9-enoic acid ethyl ester, which was hydrolyzed in step 2 to 10-(3-fluoro-phenyl)-dec-9-enoic acid. In step 3, this was converted to 10-(3-fluoro-phenyl)-dec-9-enoyl chloride, then reacted with (R)-3-amino-4-dimethylamino-butyric acid benzyl ester dihydrochloride, leading to (R)-4-dimethylamino-3-[10-(3-fluoro-phenyl)-dec-9-enoylamino]-butyric acid benzyl ester, which was hydrogenated in step 4.

Example 42

(R)-3-[10-(2,3-Difluoro-phenyl)-decanoylamino]-4-dimethylamino-butyric acid

The title compound, m/e=413.3 ([M+H]$^+$), was produced in analogy with example 34, steps 2 to 4. Thus 2,3-difluorobenzaldehyde was reacted in step 2 with (8-carboxy-octyl)-triphenyl-phosphonium bromide, leading to 10-(2,3-difluoro-phenyl)-dec-9-enoic acid. In step 3, this was converted to 10-(2,3-difluoro-phenyl)-dec-9-enoyl chloride, then reacted with (R)-3-amino-4-dimethylamino-butyric acid benzyl ester dihydrochloride, leading to (R)-4-dimethylamino-3-[10-(2,3-difluoro-phenyl)-dec-9-enoylamino]-butyric acid benzyl ester, which was hydrogenated in step 4.

Example 43

(R)-4-Dimethylamino-3-(10-thiophen-3-yl-decanoylamino)-butyric acid

Step 1: Reaction of 3-thiophenecarboxaldehyde with (8-carboxy-octyl)-triphenyl-phosphonium bromide, in analogy with example 34, step 2, produced 10-(thiophen-3-yl)-dec-9-enoic acid.

Step 2: In analogy with example 34, step 3, 10-(thiophen-3-yl)-dec-9-enoic acid was converted to 10-(thiophen-3-yl)-dec-9-enoyl chloride, then reacted with (R)-3-amino-4-dimethylamino-butyric acid benzyl ester dihydrochloride, leading to (R)-4-dimethylamino-3-[10-(thiophen-3-yl)-dec-9-enoylamino]-butyric acid benzyl ester.

Step 3: Triethylsilane (0.23 mL, 1.43 mmol) and trifluoroacetic acid (0.21 mL, 2.9 mmol) were added to a solution of 4-dimethylamino-3-(10-thiophen-3-yl-dec-9-enoylamino)-butyric acid benzyl ester (67 mg, 0.14 mmol) in toluene (8 mL). The reaction mixture was stirred at room temperature for 12 hours after which time the solution was added to cold saturated aq. sodium bicarbonate solution. The aqueous phase was separated and extracted twice with dichloromethane. The combined organics were dried over magnesium sulfate, filtered and concentrated in vacuo to afford 4-dimethylamino-3-(10-thiophen-3-yl-decanoylamino)-butyric acid benzyl ester (74 mg), m/e=473.3 ([M+H]⁺).

Step 4: Hydrolysis of 4-dimethylamino-3-(10-thiophen-3-yl-decanoylamino)-butyric acid benzyl ester, in analogy with example 35, step 2, produced (R)-4-dimethylamino-3-(10-thiophen-3-yl-decanoylamino)-butyric acid, m/e=383.1 ([M+H]⁺).

Example 44

(R)-4-Dimethylamino-3-(10-thiazol-5-yl-decanoylamino)-butyric acid

The title compound, m/e=384.3 ([M+H]⁺), was produced in analogy with example 43, steps 1 to 4. Thus, thiazole-5-carboxaldehyde was reacted in step 1 with (8-carboxy-octyl)-triphenyl-phosphonium bromide, leading to 10-(thiazol-5-yl)-dec-9-enoic acid. In step 2, this was converted to 10-(thiazol-5-yl)-dec-9-enoyl chloride, then reacted with (R)-3-amino-4-dimethylamino-butyric acid benzyl ester dihydrochloride, leading to (R)-4-dimethylamino-3-[10-(2,3-difluoro-phenyl)-dec-9-enoylamino]-butyric acid benzyl ester. In step 3, reaction of (R)-4-dimethylamino-3-[10-(2,3-difluoro-phenyl)-dec-9-enoylamino]-butyric acid benzyl ester with triethylsilane-trifluoroacetic acid produced 4-dimethylamino-3-(10-thiazol-5-yl-decanoylamino)-butyric acid benzyl ester, which was hydrolyzed in step 4.

Example 45

(R)-4-Dimethylamino-3-(6-phenyl-hexanoylamino)-butyric acid

The title compound, m/e=321.3 ([M+H]⁺), was produced in analogy with example 1, steps 3 and 4. Thus, commercially available 6-phenylhexanoic acid was coupled in step 3 with (R)-3-amino-4-dimethylamino-butyric acid benzyl ester dihydrochloride to produce (R)-4-dimethylamino-3-(6-phenyl-hexanoylamino)-butyric acid benzyl ester, which was hydrogenated in step 4.

Example 46

(R)-4-Dimethylamino-3-(7-phenyl-heptanoylamino)-butyric acid

The title compound, m/e=335.4 ([M+H]⁺), was produced in analogy with example 1, steps 3 and 4. Thus, commercially available 7-phenylheptanoic acid was coupled in step 3 with (R)-3-amino-4-dimethylamino-butyric acid benzyl ester dihydrochloride to produce (R)-4-dimethylamino-3-(7-phenyl-heptanoylamino)-butyric acid benzyl ester, which was hydrogenated in step 4.

Example 47

(R)-4-Dimethylamino-3-(8-phenyl-octanoylamino)-butyric acid

The title compound, m/e=347.4 ([M−H]⁻), was produced in analogy with example 1, steps 3 and 4. Thus, commercially available 8-phenyloctanoic acid was coupled in step 3 with (R)-3-amino-4-dimethylamino-butyric acid benzyl ester dihydrochloride to produce (R)-4-dimethylamino-3-(8-phenyl-octanoylamino)-butyric acid benzyl ester, which was hydrogenated in step 4.

Example 48

(R)-4-Dimethylamino-3-(9-phenyl-nonanoylamino)-butyric acid

The title compound, m/e=361.5 ([M−H]⁻), was produced in analogy with example 1, steps 3 and 4. Thus, commercially available 9-phenylnonanoic acid was coupled in step 3 with (R)-3-amino-4-dimethylamino-butyric acid benzyl ester dihydrochloride to produce (R)-4-dimethylamino-3-(9-phenyl-nonanoylamino)-butyric acid benzyl ester, which was hydrogenated in step 4.

Example 49

(R)-4-Dimethylamino-3-(9-pyridin-3-yl-nonanoylamino)-butyric acid

The title compound, m/e=362.3 ([M−H]⁻), was produced in analogy with example 1, steps 3 and 4. Thus, 3-pyridinenonanoic acid (U.S. Pat. No. 4,632,925) was coupled in step 3 with (R)-3-amino-4-dimethylamino-butyric acid benzyl ester dihydrochloride to produce (R)-4-dimethylamino-3-(9-pyridin-3-yl-nonanoylamino)-butyric acid benzyl ester, which was hydrogenated in step 4.

Example 50

(R)-4-Dimethylamino-3-(11-phenyl-undecanoylamino)-butyric acid

The title compound, m/e=391.5 ([M+H]⁺), was produced in analogy with example 1, steps 3 and 4. Thus, commercially available 11-phenylundecanoic acid was coupled in step 3 with (R)-3-amino-4-dimethylamino-butyric acid benzyl ester dihydrochloride to produce (R)-4-dimethylamino-3-(11-phenyl-undecanoylamino)-butyric acid benzyl ester, which was hydrogenated in step 4.

Example 51

(R)-4-Dimethylamino-3-(12-phenyl-dodecanoylamino)-butyric acid

The title compound, m/e=403.6 ([M−H]⁻), was produced in analogy with example 1, steps 3 and 4. Thus, commercially available 12-phenyldodecanoic acid was coupled in step 3 with (R)-3-amino-4-dimethylamino-butyric acid benzyl ester dihydrochloride to produce (R)-4-dimethylamino-3-(12-phenyl-dodecanoylamino)-butyric acid benzyl ester, which was hydrogenated in step 4.

Example 52

(R)-4-Dimethylamino-3-[4-(5-phenyl-pentyloxy)-butyrylamino]-butyric acid

Step 1: Sodium hydride (60% dispersion in mineral oil, 228 mg, 5.7 mmol) was added to a solution of sodium 4-hydroxybutyrate (600 mg, 4.76 mmol) in N,N-dimethylformamide (5 mL). The reaction was heated at 60° C. for 1 h, then (5-bromopentyl)-benzene (1.15 g, 5.08 mmol) was added, then after 3 weeks 1 M aq. hydrochloric acid solution was added and the reaction mixture evaporated. Chromatography (SiO₂; heptane-ethyl acetate gradient) produced 4-(5-phenyl-pentyloxy)-butyric acid (32 mg, 3%) as a colorless oil.

Step 2: Amide coupling of 4-(5-phenyl-pentyloxy)-butyric acid with (R)-3-amino-4-dimethylamino-butyric acid benzyl ester dihydrochloride in analogy with example 1, step 3 led to (R)-4-dimethylamino-3-[4-(5-phenyl-pentyloxy)-butyrylamino]-butyric acid benzyl ester.

Step 3: Hydrogenation of (R)-4-dimethylamino-3-[4-(5-phenyl-pentyloxy)-butyrylamino]-butyric acid benzyl ester in analogy with example 1, step 4 produced (R)-4-dimethylamino-3-[9-(2-fluoro-phenoxy)-nonanoylamino]-butyric acid. White solid, m/e=379.5 ([M+H]$^+$).

Example 53

(R)-4-Dimethylamino-3-[6-(3-phenyl-propoxy)-hexanoylamino]-butyric acid

The title compound, m/e=379.4 ([M+H]$^+$), was produced in analogy with example 1, steps 1 to 4. Thus, 1,6-hexanediol was alkylated in step 1 with 1-bromo-3-phenylpropane, leading to 6-(3-phenyl-propoxy)-hexan-1-ol, which was oxidized in step 2 to 6-(3-phenyl-propoxy)-hexanoic acid. This was coupled in step 3 with (R)-3-amino-4-dimethylamino-butyric acid benzyl ester dihydrochloride to produce (R)-4-dimethylamino-3-[6-(3-phenyl-propoxy)-hexanoylamino]-butyric acid benzyl ester, which was hydrogenated in step 4.

Example 54

(R)-4-Dimethylamino-3-(9-phenethyloxy-nonanoylamino)-butyric acid

Step 1: A solution of 9-bromo-1-nonanol (2.00 g, 8.96 mmol), 3,4-dihydro-2H-pyran (792 mg, 9.41 mmol), and pyridinium toluene-4-sulfonate (1.08 g, 4.30 mmol) in dichloromethane (34 mL) was stirred at room temperature for 16 h, then washed with 2 M aq. sodium carbonate solution and brine, dried over sodium sulfate, filtered, and evaporated. Chromatography (SiO$_2$; heptane-ethyl acetate gradient) produced 2-(9-bromo-nonyloxy)-tetrahydro-pyran (2.45 g, 89%). Colorless oil, m/e=324.1 ([M+NH$_4$]).

Step 2: Sodium hydride (60% dispersion in mineral oil, 264 mg, 6.6 mmol) was added at 0° C. to a solution of 2-phenylethanol (807 mg, 6.61 mmol) in tetrahydrofuran (8.6 mL) and N,N-dimethylformamide (3.4 mL), then after 1 h a solution of 2-(9-bromo-nonyloxy)-tetrahydro-pyran (2.44 g, 7.93 mmol) in N,N-dimethylformamide (1.5 mL) was added dropwise. The solution was allowed to reach room temperature over 16 h, then partitioned between water and ethyl acetate. The organic layer was washed with brine, dried over sodium sulfate, filtered, and evaporated. Chromatography (SiO$_2$; heptane-ethyl acetate gradient) produced 2-(9-phenethyloxy-nonyloxy)-tetrahydro-pyran (898 mg, 39%). Colorless oil, m/e=366.2 ([M+NH$_4$]$^+$).

Step 3: A solution of 2-(9-phenethyloxy-nonyloxy)-tetrahydro-pyran (890 mg, 2.55 mmol) in acetic acid/tetrahydrofuran/water 4:2:1 (23 mL) was stirred at 45° C. for 4 h. After evaporation, the residue was purified by chromatography (SiO$_2$; heptane-ethyl acetate gradient), affording 9-phenethyloxy-nonan-1-ol (513 mg, 76%). Colorless oil, m/e=265.3 ([M+H]$^+$).

Step 4: Oxidation of 9-phenethyloxy-nonan-1-ol in analogy with example 1, step 2 gave 9-phenethyloxy-nonanoic acid. White solid, m/e=277.4 ([M−H]$^-$).

Step 5: Amide coupling of 9-phenethyloxy-nonanoic acid with (R)-3-amino-4-dimethylamino-butyric acid benzyl ester dihydrochloride in analogy with example 1, step 3 led to (R)-4-dimethylamino-3-(9-phenethyloxy-nonanoylamino)-butyric acid benzyl ester. Light yellow oil, m/e=497.5 ([M+H]$^+$).

Step 6: Hydrogenation of (R)-4-dimethylamino-3-(9-phenethyloxy-nonanoylamino)-butyric acid benzyl ester in analogy with example 1, step 4 produced (R)-4-dimethylamino-3-[9-(2-fluoro-phenoxy)-nonanoylamino]-butyric acid. White solid, m/e=405.6 ([M−H]$^-$).

Example 55

(R)-4-Dimethylamino-3-[8-(3-phenyl-propoxy)-octanoylamino]-butyric acid

The title compound, m/e=405.7 ([M−H]$^-$), was produced in analogy with example 54, steps 1 to 6. Thus, 8-bromo-1-octanol was protected in step 1, leading to 2-(8-bromo-octyloxy)-tetrahydro-pyran, which was reacted in step 2 with 3-phenoxypropanol, affording 2-(8-(3-phenyl-propoxy)-octyloxy)-tetrahydro-pyran, which after deprotection in step 3 gave 8-(3-phenyl-propoxy)-octan-1-ol. This was oxidized in step 4 to 8-(3-phenyl-propoxy)-octanoic acid, which was coupled in step 5 with (R)-3-amino-4-dimethylamino-butyric acid benzyl ester dihydrochloride, leading to (R)-4-dimethylamino-3-[8-(3-phenyl-propoxy)-octanoylamino]-butyric acid benzyl ester, which was hydrogenated in step 6.

Example 56

(R)-4-Dimethylamino-3-[8-(2-phenoxy-ethoxy)-octanoylamino]-butyric acid

The title compound, m/e=407.6 ([M−H]$^-$), was produced in analogy with example 54, steps 1 to 6. Thus, 8-bromo-1-octanol was protected in step 1, leading to 2-(8-bromo-octyloxy)-tetrahydro-pyran, which was reacted in step 2 with 2-phenoxyethanol, affording 2-(8-(2-phenoxy-ethoxy)-octyloxy)-tetrahydro-pyran, which after deprotection in step 3 gave 8-(2-phenoxy-ethoxy)-octan-1-ol. This was oxidized in step 4 to 8-(2-phenoxy-ethoxy)-octanoic acid, which was coupled in step 5 with (R)-3-amino-4-dimethylamino-butyric acid benzyl ester dihydrochloride, leading to (R)-4-dimethylamino-3-[8-(2-phenoxy-ethoxy)-octanoylamino]-butyric acid benzyl ester, which was hydrogenated in step 6.

Example 57

(R)-3-(10-Benzyloxy-decanoylamino)-4-dimethylamino-butyric acid

The title compound, m/e=405.6 ([M−H]$^-$), was produced in analogy with example 1, steps 1 to 4. Thus, 1,10-decanediol was alkylated in step 1 with benzyl bromide, leading to 10-benzyloxy-decan-1-ol, which was oxidized in step 2 to 10-benzyloxydecanoic acid. This was coupled in step 3 with (R)-3-amino-4-dimethylamino-butyric acid benzyl ester dihydrochloride to produce (R)-3-(10-benzyloxy-decanoylamino)-4-dimethylamino-butyric acid benzyl ester, which was hydrogenated in step 4.

Example 58

(R)-4-Dimethylamino-3-[7-(2-phenyl-ethanesulfonyl)-heptanoylamino]-butyric acid

Step 1: 2-Phenylethanethiol was alkylated with 7-bromo-1-heptanol in analogy with example 18, step 1, affording 7-phenethylsulfanyl-heptan-1-ol.

Step 2: Oxone® (3.3 g, 5.5 mmol) was added to a solution of 7-phenethylsulfanyl-heptan-1-ol (930 mg, 3.68 mmol) in methanol (40 mL), then after 16 h insoluble material was removed by filtration and the filtrate evaporated, affording 7-(2-phenyl-ethanesulfonyl)-heptan-1-ol (1.6 g), which was directly used in the next step.

Step 3: Oxidation of 7-(2-phenyl-ethanesulfonyl)-heptan-1-ol in analogy with example 1, step 2 gave 7-(2-phenyl-ethanesulfonyl)-heptanoic acid.

Step 4: Amide coupling of 7-(2-phenyl-ethanesulfonyl)-heptanoic acid with (R)-3-amino-4-dimethylamino-butyric acid benzyl ester dihydrochloride in analogy with example 1, step 3 led to (R)-4-dimethylamino-3-[7-(2-phenyl-ethanesulfonyl)-heptanoylamino]-butyric acid benzyl ester.

Step 5: Hydrogenation of (R)-4-dimethylamino-3-[7-(2-phenyl-ethanesulfonyl)-heptanoylamino]-butyric acid benzyl ester in analogy with example 1, step 4 produced (R)-4-dimethylamino-3-[7-(2-phenyl-ethanesulfonyl)-heptanoylamino]-butyric acid. White solid, m/e=427.3 ([M+H]$^+$).

Example 59

(R)-4-Dimethylamino-3-(8-(phenylmethanesulfonyl)-octanoylamino)-butyric acid

The title compound, m/e=427.4 ([M+H]$^+$), was produced in analogy with example 59, steps 1 to 5. Thus, phenylmethanethiol was alkylated in step 1 with 8-bromo-1-octanol, leading to 8-benzylsulfanyl-octan-1-ol, which was oxidized in step 2 to 8-phenylmethanesulfonyl-octan-1-ol. This was oxidized in step 3 to 8-phenylmethanesulfonyl-octanoic acid, then coupled in step 4 with (R)-3-amino-4-dimethylamino-butyric acid benzyl ester dihydrochloride to produce (R)-4-dimethylamino-3-(8-(phenylmethanesulfonyl)-octanoylamino)-butyric acid benzyl ester, which was hydrogenated in step 5.

Example 60

(R)-3-(9-Benzenesulfonyl-nonanoylamino)-4-dimethylamino-butyric acid

The title compound, m/e=427.5 ([M+H]$^+$), was produced in analogy with example 18, steps 1 to 4. Thus, benzenesulfinic acid sodium salt was alkylated in step 1 with 9-bromo-1-nonanol, leading to 9-benzenesulfonyl-nonan-1-ol, which was oxidized in step 2 to 9-benzenesulfonyl-nonanoic acid. This was coupled in step 3 with (R)-3-amino-4-dimethylamino-butyric acid benzyl ester dihydrochloride to produce (R)-3-(9-benzenesulfonyl-nonanoylamino)-4-dimethylamino-butyric acid benzyl ester, which was hydrogenated in step 4.

Example 61

(R)-3-{7-[2-(2,3-Difluoro-phenyl)-ethoxy]-heptanoylamino}-4-dimethylamino-butyric acid The title compound, m/e=413.5 ([M−H]$^-$), was produced in analogy with example 54, steps 1 to 6. Thus, 7-bromo-1-heptanol was protected in step 1, leading to 2-(7-bromo-heptyloxy)-tetrahydro-pyran, which was reacted in step 2 with 2-(2,3-difluorophenoxy)-ethanol, affording 2-(7-[2-(2,3-difluoro-phenyl)-ethoxy]-heptyloxy)-tetrahydro-pyran, which after deprotection in step 3 gave 7-[2-(2,3-difluoro-phenyl)-ethoxy]-heptan-1-ol. This was oxidized in step 4 to 7-[2-(2,3-difluoro-phenyl)-ethoxy]-heptanoic acid, which was coupled in step 5 with (R)-3-amino-4-dimethylamino-butyric acid benzyl ester dihydrochloride, leading to (R)-3-{7-[2-(2,3-difluoro-phenyl)-ethoxy]-heptanoylamino}-4-dimethylamino-butyric acid benzyl ester, which was hydrogenated in step 6.

Example 62

(R)-3-{3-[6-(2,3-Difluoro-benzyloxy)-hexyl]-ureido}-4-dimethylamino-butyric acid Step 1: Ethyl chloroformate (414 mg, 3.82 mmol) was added at 0° C. to a solution of 7-[2-(2,3-difluoro-phenyl)-ethoxy]-heptanoic acid (800 mg, 2.94 mmol) and triethylamine (387 mg, 3.82 mmol) in dichloromethane (15 mL), then after 2 h volatile material was removed by distillation, producing 7-[2-(2,3-difluoro-phenyl)-ethoxy]-heptanoyl chloride (855 mg). This was redissolved in acetone (2 mL) and treated at 0° C. with a solution of sodium azide (268 mg, 4.12 mmol) in water (4 mL) under vigorous stirring. The reaction mixture was stirred for 1 h at 10° C., then partitioned between toluene and brine. The organic layer was separated and heated at 65° C. for 90 min, then concentrated in vacuo, affording [6-(2,3-difluoro-benzyloxy)-hexyl]-isocyanate (486 mg, 61%) as a yellow oil.

Step 2: A solution of [6-(2,3-difluoro-benzyloxy)-hexyl]-isocyanate (224 mg, 0.83 mmol) in dichloromethane (1 mL) was added at 0° C. to a suspension of (R)-3-amino-4-dimethylamino butyric acid benzyl ester dihydrochloride (255 mg, 0.83 mmol) in dichloromethane (4 mL), then a solution of triethylamine (167 mg, 1.65 mmol) in dichloromethane (1 mL) was added dropwise over 25 min. The reaction mixture was kept at <5° C. for 1 h, then allowed to reach room temperature over 1 h. Insoluble material was removed by filtration and the filtrate evaporated. The residue was purified by preparative HPLC to afford (R)-3-{3-[6-(2,3-difluoro-benzyloxy)-hexyl]-ureido}-4-dimethylamino-butyric acid benzyl ester (56 mg, 13%) as a colorless oil.

Step 3: Hydrogenation of (R)-3-{3-[6-(2,3-difluoro-benzyloxy)-hexyl]-ureido}-4-dimethylamino-butyric acid benzyl ester in analogy with example 1, step 4 produced (R)-3-{3-[6-(2,3-difluoro-benzyloxy)-hexyl]-ureido}-4-dimethylamino-butyric acid. Colorless oil, m/e=414.4 ([M+H]$^+$).

Example 63

(R)-4-Dimethylamino-3-[3-(9-phenyl-nonyl)-ureido]-butyric acid

The title compound, m/e=392.4 ([M+H]$^+$), was produced in analogy with example 62, steps 1 to 3. Thus 10-phenyldecanoic acid was elaborated in step 1 to 9-phenyl-nonyl-isocyanate. This was coupled in step 2 with (R)-3-amino-4-dimethylamino-butyric acid benzyl ester dihydrochloride, leading to (R)-4-dimethylamino-3-[3-(9-phenyl-nonyl)-ureido]-butyric acid benzyl ester, which was hydrogenated in step 3.

Example 64

(R)-4-Dimethylamino-3-[9-(methyl-phenethyl-amino)-nonanoylamino]-butyric acid

Step 1: To a solution of 9-oxononanoic acid methyl ester (*J. Org. Chem.* 2007, 72, 9471; 303 mg, 1.63 mmol) and N-methyl-2-phenylethylamine (220 mg, 1.63 mmol) in methanol (10 mL) was added concentrated sulfuric acid (5 drops) at room temperature, then after 40 h the solution was heated at reflux for 2 h. After cooling sodium borohydride (123 mg, 3.25 mmol) was added, then after 1 h the reaction mixture was partitioned between water and dichloromethane. The organic layer was dried over sodium sulfate, filtered, and evaporated to afford 9-(methyl-phenethyl-amino)-nonanoic acid methyl ester as a light yellow liquid.

Step 2: 9-(Methyl-phenethyl-amino)-nonanoic acid methyl ester was hydrolyzed in analogy with example 35, step 2, leading to 9-(methyl-phenethyl-amino)-nonanoic acid.

Step 3: Amide coupling of 9-(methyl-phenethyl-amino)-nonanoic acid with (R)-3-amino-4-dimethylamino-butyric acid benzyl ester dihydrochloride in analogy with example 1, step 3, led to (R)-4-dimethylamino-3-[9-(methyl-phenethyl-amino)-nonanoylamino]-butyric acid benzyl ester.

Step 4: Hydrogenation of (R)-4-dimethylamino-3-[9-(methyl-phenethyl-amino)-nonanoylamino]-butyric acid benzyl ester in analogy with example 1, step 4 produced (R)-4-dimethylamino-3-[9-(methyl-phenethyl-amino)-nonanoylamino]-butyric acid. Colorless liquid, m/e=420.3 ([M+H]$^+$).

Example 65

(R)-4-Dimethylamino-3-(9-phenethylamino-nonanoylamino)-butyric acid

The title compound, m/e=406.6 ([M+H]$^+$), was produced in analogy with example 64, steps 1 to 4. Thus, 9-oxononanoic acid methyl ester was reacted in step 1 with N-benzyl-2-phenylethylamine, leading to 9-(benzyl-phenethyl-amino)-nonanoic acid methyl ester, which was hydrolyzed in step 2 to afford 9-(benzyl-phenethyl-amino)-nonanoic acid. This was coupled in step 3 with (R)-3-amino-4-dimethylamino-butyric acid benzyl ester dihydrochloride, leading to (R)-3-[9-(benzyl-phenethyl-amino)-nonanoylamino]-4-dimethylamino-butyric acid benzyl ester, which was hydrogenated in step 4.

Example 66

(R)-4-Dimethylamino-3-[9-(methyl-phenyl-amino)-nonanoylamino]-butyric acid

Step 1: Azelaic acid monomethyl ester was coupled with N-methylaniline in analogy with example 1, step 3, leading to 8-(methyl-phenyl-carbamoyl)-octanoic acid methyl ester.

Step 2: Borane-tetrahydrofuran complex (1 M in tetrahydrofuran, 3.09 mL, 3.09 mmol) was added at 0° C. to a solution of 8-(methyl-phenyl-carbamoyl)-octanoic acid methyl ester (300 mg, 1.03 mmol) in tetrahydrofuran (20 mL) The reaction mixture was stirred at room temperature overnight. A further aliquot of borane-tetrahydrofuran complex (2.1 mL, 2.1 mmol) was added and the reaction mixture was stirred at room temperature for 3.5 hours. Methanol (60 mL) was added followed by concentrated sulfuric acid. The reaction mixture was refluxed at 80° C. for 2 hours. After cooling to room temperature, saturated sodium carbonate was added and the reaction mixture was extracted 3 times with dichloromethane. The combined organic layers were dried over sodium sulfphate, filtered and the solvent was removed in vacuo. The crude product was purified by chromatography (SiO$_2$; heptane-ethyl acetate gradient) to afford 9-(methyl-phenyl-amino)-nonanoic acid methyl ester (89 mg, 31%).

Step 3: 9-(Methyl-phenyl-amino)-nonanoic acid methyl ester was hydrolyzed in analogy with example 35, step 2, leading to 9-(methyl-phenyl-amino)-nonanoic acid.

Step 4: Amide coupling of 9-(methyl-phenyl-amino)-nonanoic acid with (R)-3-amino-4-dimethylamino-butyric acid benzyl ester dihydrochloride in analogy with example 1, step 3 led to (R)-4-dimethylamino-3-[9-(methyl-phenyl-amino)-nonanoylamino]-butyric acid benzyl ester.

Step 5: Hydrogenation of (R)-4-dimethylamino-3-[9-(methyl-phenyl-amino)-nonanoylamino]-butyric acid benzyl ester in analogy with example 1, step 4 produced (R)-4-dimethylamino-3-[9-(methyl-phenethyl-amino)-nonanoylamino]-butyric acid. White solid, m/e=392.3 ([M+H]$^+$).

Example A

Film coated tablets containing the following ingredients can be manufactured in a conventional manner:

| Ingredients | Per tablet | |
|---|---|---|
| Kernel: | | |
| Compound of formula (I) | 10.0 mg | 200.0 mg |
| Microcrystalline cellulose | 23.5 mg | 43.5 mg |
| Lactose hydrous | 60.0 mg | 70.0 mg |
| Polyvinylpyrrolidone K30 | 12.5 mg | 15.0 mg |
| Sodium starch glycolate | 12.5 mg | 17.0 mg |
| Magnesium stearate | 1.5 mg | 4.5 mg |
| (Kernel Weight) | 120.0 mg | 350.0 mg |
| Film Coat: | | |
| Hydroxypropyl methyl cellulose | 3.5 mg | 7.0 mg |
| Polyethylene glycol 6000 | 0.8 mg | 1.6 mg |
| Talc | 1.3 mg | 2.6 mg |
| Iron oxide (yellow) | 0.8 mg | 1.6 mg |
| Titanium dioxide | 0.8 mg | 1.6 mg |

The active ingredient is sieved and mixed with microcrystalline cellulose and the mixture is granulated with a solution of polyvinylpyrrolidon in water. The granulate is mixed with sodium starch glycolate and magesiumstearate and compressed to yield kernels of 120 or 350 mg respectively. The kernels are lacquered with an aqueous solution/suspension of the above mentioned film coat.

Example B

Capsules containing the following ingredients can be manufactured in a conventional manner:

| Ingredients | Per capsule |
|---|---|
| Compound of formula (I) | 25.0 mg |
| Lactose | 150.0 mg |
| Maize starch | 20.0 mg |
| Talc | 5.0 mg |

The components are sieved and mixed and filled into capsules of size 2.

Example C

Injection solutions can have the following composition:

| | |
|---|---|
| Compound of formula (I) | 3.0 mg |
| Polyethylene glycol 400 | 150.0 mg |
| Acetic acid | q.s. ad pH 5.0 |
| Water for injection solutions | ad 1.0 ml |

The active ingredient is dissolved in a mixture of polyethylene glycol 400 and water for injection (part). The pH is adjusted to 5.0 with acetic acid. The volume is adjusted to 1.0 ml by addition of the residual amount of water. The solution is filtered, filled into vials using an appropriate overage and sterilized.

Example D

Soft gelatin capsules containing the following ingredients can be manufactured in a conventional manner:

| | |
|---|---|
| Capsule contents | |
| Compound of formula (I) | 5.0 mg |
| Yellow wax | 8.0 mg |
| Hydrogenated Soya bean oil | 8.0 mg |
| Partially hydrogenated plant oils | 34.0 mg |
| Soya bean oil | 110.0 mg |
| Weight of capsule contents | 165.0 mg |
| Gelatin capsule | |
| Gelatin | 75.0 mg |
| Glycerol 85% | 32.0 mg |
| Karion 83 | 8.0 mg (dry matter) |
| Titanium dioxide | 0.4 mg |
| Iron oxide yellow | 1.1 mg |

The active ingredient is dissolved in a warm melting of the other ingredients and the mixture is filled into soft gelatin capsules of appropriate size. The filled soft gelatin capsules are treated according to the usual procedures.

Example E

Sachets containing the following ingredients can be manufactured in a conventional manner:

| | |
|---|---|
| Compound of formula (I) | 50.0 mg |
| Lactose, fine powder | 1015.0 mg |
| Microcrystalline cellulose (AVICEL PH 102) | 1400.0 mg |
| Sodium carboxymethyl cellulose | 14.0 mg |
| Polyvinylpyrrolidone K 30 | 10.0 mg |
| Magnesium stearate | 10.0 mg |
| Flavoring additives | 1.0 mg |

The active ingredient is mixed with lactose, microcrystalline cellulose and sodium carboxymethyl cellulose and granulated with a mixture of polyvinylpyrrolidone in water. The granulate is mixed with magnesiumstearate and the flavoring additives and filled into sachets.

The invention claimed is:

1. A compound of the formula

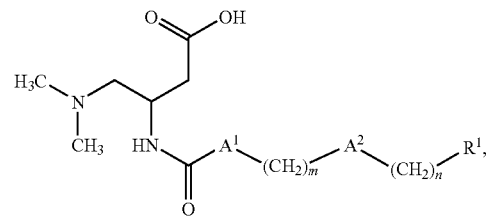

wherein
A$^1$ is a bond,
A$^2$ is selected from the group consisting of a bond, O, O(CH$_2$)$_2$O, S, SO$_2$, CF$_2$ and NR$^2$, wherein R$^2$ is hydrogen or lower alkyl,
m is selected from 2, 3, 4, 5, 6, 7, 8, 9, 10 and 11,
n is selected from 0, 1, 2, 3, 4 and 5,
R$^1$ is aryl selected from phenyl and naphthyl, said aryl being unsubstituted or substituted by one, two, three, four or five groups selected from the group consisting of lower alkyl, halogen, lower halogenalkyl, lower alkoxy and phenyl, or
heteroaryl selected from the group consisting of pyridyl, thienyl and thiazolyl, said heteroaryl being unsubstituted or substituted by one, two or three groups selected from lower alkyl, halogen, lower halogenalkyl, lower alkoxy and phenyl, and pharmaceutically acceptable salts thereof.

2. The compound of formula I according to claim 1, wherein A$^2$ is selected from the group consisting of a bond, O, O(CH$_2$)$_2$O, S, SO$_2$ and NR$^2$, wherein R$^2$ is hydrogen or lower alkyl.

3. The compound of formula I according to claim 2, wherein A$^2$ is selected from the group consisting of a bond, O and O(CH$_2$)$_2$O.

4. The compound of formula I according to claim 3, wherein A$^2$ is O or O(CH$_2$)$_2$O.

5. The compound of formula I according to claim 3, wherein A$^2$ is a bond.

6. The compound of formula I according to claim 1, wherein m is selected from 6, 7, 8, 9, 10 and 11.

7. The compound of formula I according to claim 1, wherein n is selected from 0, 1, 2 and 3.

8. The compound of formula I according to claim 7, wherein n is selected from 0 or 1.

9. The compound of formula I according to claim 1, wherein R$^1$ is aryl selected from phenyl and naphthyl, said aryl being unsubstituted or substituted by one, two, three, four or five groups selected from the group consisting of lower alkyl, halogen, lower halogenalkyl, lower alkoxy and phenyl.

10. The compounds of formula I according to claim 9, wherein R$^1$ is phenyl substituted by one, two, three, four or five groups selected from the group consisting of lower alkyl, halogen, lower halogenalkyl, lower alkoxy and phenyl, provided that at least one of the substituents is halogen or lower halogenalkyl.

11. The compound of formula I according to claim 1, wherein R$^1$ is heteroaryl selected from the group consisting of pyridyl, thienyl and thiazolyl, said heteroaryl being unsubstituted or substituted by one, two or three groups selected from lower alkyl, halogen, lower halogenalkyl, lower alkoxy and phenyl.

12. The compound of formula I according to claim 11, wherein $R^1$ is heteroaryl selected from the group consisting of pyridyl, thienyl and thiazolyl.

13. A compound of formula I according to claim 1 having the formula

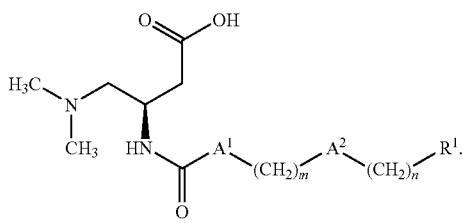

I-A

14. A compound of formula I according to claim 1, which is (R)-4-dimethylamino-3-(10-phenyl-decanoylamino)-butyric acid.

15. A process for the preparation of compounds of formula I as defined in claim 1, which process comprises
 a) condensating an amine of formula

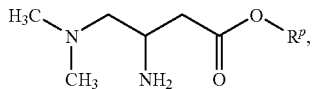

II wherein $R^p$ is methyl, ethyl or benzyl, with a carboxylic acid of the formula

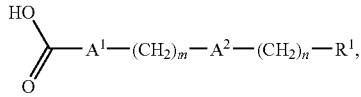

III wherein $A^1$ is a bond and $A^2$, m, n and $R^1$ are as defined in claim 1,
in the presence of a base and a condensing agent to obtain a compound of the formula

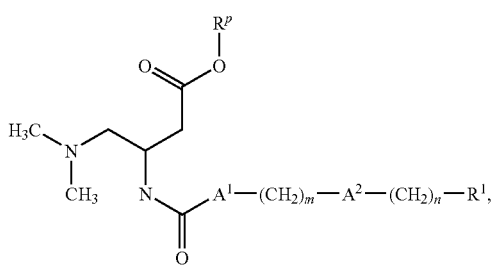

IV and transforming the compound of formula IV into a compound of formula I, wherein $A^1$ is a bond, by ester hydrolysis or hydrogenation.

16. A process for the preparation of compounds of formula I as defined in claim 1, which process comprises
 a) condensating the amine of formula

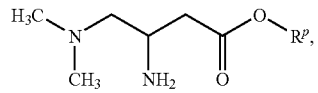

II wherein $R^p$ is methyl, ethyl or benzyl, with an isocyanate of the formula

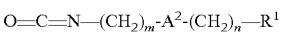

O=C=N—(CH$_2$)$_m$-A$^2$-(CH$_2$)$_n$—R$^1$  V, wherein $A^2$, m, n and $R^1$ are as defined in claim 1,
in the presence of a base to obtain a compound of the formula

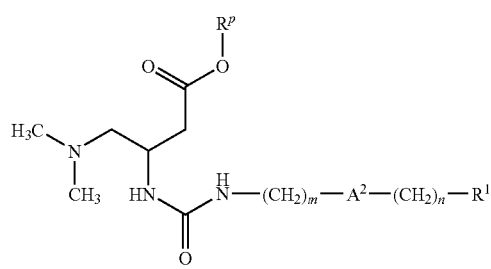

VI and transforming the compound of formula VI into a compound of formula I, wherein $A^1$ is NH, by ester hydrolysis or hydrogenation.

17. A process for the preparation of compounds of formula I as defined in claim 1, which process comprises
 a) condensating the amine of formula

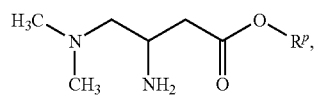

II wherein $R^p$ is benzyl, with a carboxylic acid of the formula

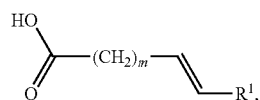

VII wherein m and $R^1$ are as defined in claim 1,
in the presence of a base and a condensing agent to obtain a compound of the formula

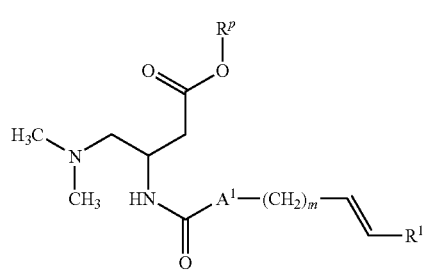

VIII and transforming the compound of formula VIII into a compound of formula I, wherein $A^2$ is a bond and n is 2, by hydrogenation.

18. A pharmaceutical composition comprising a compound of formula I according to claim 1 and a pharmaceutically acceptable carrier and/or adjuvant.

19. A method for the treatment of diseases which are modified by CPT2 inhibitors, comprising administering a compound of formula I according to claim 1 to a human being or animal.

20. A method for the therapeutic treatment of diseases which are modulated by CPT2 inhibitors, wherein the diseases are selected from hyperglycemia, glucose tolerance disorders, diabetes and associated pathologies, non insulin dependent diabetes mellitus, obesity, hypertension, insulin resistance syndrome, metabolic syndrome, hyperlipidemia, hypercholesterolemia, fatty liver disease, atherosclerosis, congestive heart failure and renal failure, which method comprises administering a compound of formula I according to claim 1 to a human being or animal.

21. A method for the therapeutic treatment of hyperglycemia and non-insulin dependent diabetes mellitus, comprising administering a compound of formula I according to claim 1 to a human being or animal.

22. A compound of formula I according to claim 1, selected from the group consisting of
 (R)-3-[8-(3,4-difluoro-benzyloxy)-octanoylamino]-4-dimethylamino-butyric acid,
 (R)-3-[8-(2,5-difluoro-benzyloxy)-octanoylamino]-4-dimethylamino-butyric acid,
 (R)-3-[8-(2,4-difluoro-benzyloxy)-octanoylamino]-4-dimethylamino-butyric acid,
 (R)-4-dimethylamino-3-[8-(2,3,4-trifluoro-benzyloxy)-octanoylamino]-butyric acid,
 (R)-4-dimethylamino-3-(8-pentafluorophenylmethoxy-octanoylamino)-butyric acid,
 (R)-4-dimethylamino-3-[8-(4-trifluoromethyl-benzyloxy)-octanoylamino]-butyric acid,
 (R)-4-dimethylamino-3-[8-(3-fluoro-4-trifluoromethyl-benzyloxy)-octanoylamino]-butyric acid,
 (R)-4-dimethylamino-3-[8-(4-methoxy-benzyloxy)-octanoylamino]-butyric acid,
 (R)-3-[8-(biphenyl-4-ylmethoxy)-octanoylamino]-4-dimethylamino-butyric acid,
 (R)-4-dimethylamino-3-[8-(2-fluoro-4-trifluoromethyl-benzyloxy)-octanoylamino]-butyric acid, and pharmaceutically acceptable salts thereof.

23. A compound of formula I according to claim 1, selected from the group consisting of
 (R)-4-dimethylamino-3-[8-(2,3,5,6-tetrafluoro-4-methoxy-benzyloxy)-octanoylamino]-butyric acid,
 (R)-4-dimethylamino-3-[8-(naphthalen-1-ylmethoxy)-octanoylamino]-butyric acid,
 (R)-4-dimethylamino-3-[8-(2-fluoro-benzyloxy)-octanoylamino]-butyric acid,
 (R)-4-dimethylamino-3-[8-(3-fluoro-benzyloxy)-octanoylamino]-butyric acid,
 (R)-4-dimethylamino-3-[8-(4-fluoro-benzyloxy)-octanoylamino]-butyric acid,
 (R)-3-[8-(2,3-difluoro-benzyloxy)-octanoylamino]-4-dimethylamino-butyric acid,
 (R)-3-(8-benzyloxy-octanoylamino)-4-dimethylamino-butyric acid,
 (R)-4-dimethylamino-3-[9-(2-fluoro-phenoxy)-nonanoylamino]-butyric acid,
 (R)-4-dimethylamino-3-[9-(3-fluoro-phenoxy)-nonanoylamino]-butyric acid,
 (R)-4-dimethylamino-3-[9-(4-fluoro-phenoxy)-nonanoylamino]-butyric acid,
and pharmaceutically acceptable salts thereof.

24. A compound of formula I according to claim 1, selected from the group consisting of
 (R)-3-[9-(2,3-difluoro-phenoxy)-nonanoylamino]-4-dimethylamino-butyric acid,
 (R)-3-[9-(2,4-difluoro-phenoxy)-nonanoylamino]-4-dimethylamino-butyric acid,
 (R)-3-[9-(3,4-difluoro-phenoxy)-nonanoylamino]-4-dimethylamino-butyric acid,
 (R)-4-dimethylamino-3-[9-(2,3,4-trifluoro-phenoxy)-nonanoylamino]-butyric acid,
 (R)-3-[9-(biphenyl-4-yloxy)-nonanoylamino]-4-dimethylamino-butyric acid,
 (R)-3-[9-(3,4-dimethoxy-phenoxy)-nonanoylamino]-4-dimethylamino-butyric acid,
 (R)-4-dimethylamino-3-[9-(4-trifluoromethyl-phenoxy)-nonanoylamino]-butyric acid,
 (R)-4-dimethylamino-3-[9-(4-methoxy-phenoxy)-nonanoylamino]-butyric acid,
 (R)-4-dimethylamino-3-[9-(naphthalen-1-yloxy)-nonanoylamino]-butyric acid,
 (R)-4-dimethylamino-3-(11-phenoxy-undecanoylamino)-butyric acid,
and pharmaceutically acceptable salts thereof.

25. A compound of formula I according to claim 1, selected from the group consisting of
 (R)-4-dimethylamino-3-(9-phenoxy-nonanoylamino)-butyric acid,
 (R)-4-dimethylamino-3-(10-phenyl-decanoylamino)-butyric acid,
 (S)-4-dimethylamino-3-(10-phenyl-decanoylamino)-butyric acid,
 (R)-4-dimethylamino-3-[10-(4-fluoro-phenyl)-decanoylamino]-butyric acid,
 (R)-4-dimethylamino-3-[10-(2-fluoro-phenyl)-decanoylamino]-butyric acid,
 (R)-4-dimethylamino-3-[10-(2,5-dimethyl-phenyl)-decanoylamino]-butyric acid,
 (R)-4-dimethylamino-3-[10-(2,6-dimethyl-phenyl)-decanoylamino]-butyric acid,
 (R)-4-dimethylamino-3-[10-(4-methoxy-phenyl)-decanoylamino]-butyric acid,
 (R)-4-dimethylamino-3-(10-naphthalen-1-yl-decanoylamino)-butyric acid,
 (R)-4-dimethylamino-3-[10-(4-trifluoromethyl-phenyl)-decanoylamino]-butyric acid,
and pharmaceutically acceptable salts thereof.

26. A compound of formula I according to claim 1, selected from the group consisting of
 (R)-4-dimethylamino-3-[10-(3-fluoro-phenyl)-decanoylamino]-butyric acid,
 (R)-3-[10-(2,3-difluoro-phenyl)-decanoylamino]-4-dimethylamino-butyric acid,
 (R)-4-dimethylamino-3-(10-thiophen-3-yl-decanoylamino)-butyric acid,
 (R)-4-dimethylamino-3-(10-thiazol-5-yl-decanoylamino)-butyric acid,
 (R)-4-dimethylamino-3-(6-phenyl-hexanoylamino)-butyric acid,
 (R)-4-dimethylamino-3-(7-phenyl-heptanoylamino)-butyric acid,
 (R)-4-dimethylamino-3-(8-phenyl-octanoylamino)-butyric acid,
 (R)-4-dimethylamino-3-(9-phenyl-nonanoylamino)-butyric acid, (R)-4-dimethylamino-3-(9-pyridin-3-yl-nonanoylamino)-butyric acid,
(R)-4-dimethylamino-3-(11-phenyl-undecanoylamino)-butyric acid,
and pharmaceutically acceptable salts thereof.

27. A compound of formula I according to claim 1, selected from the group consisting of
(R)-4-dimethylamino-3-(12-phenyl-dodecanoylamino)-butyric acid,
(R)-4-dimethylamino-3-[4-(5-phenyl-pentyloxy)-butyrylamino]-butyric acid,
(R)-4-dimethylamino-3-[6-(3-phenyl-propoxy)-hexanoylamino]-butyric acid,
(R)-4-dimethylamino-3-(9-phenethyloxy-nonanoylamino)-butyric acid,
(R)-4-dimethylamino-3-[8-(3-phenyl-propoxy)-octanoylamino]-butyric acid,
(R)-4-dimethylamino-3-[8-(2-phenoxy-ethoxy)-octanoylamino]-butyric acid,
(R)-3-(10-benzyloxy-decanoylamino)-4-dimethylamino-butyric acid,
(R)-4-dimethylamino-3-[7-(2-phenyl-ethanesulfonyl)-heptanoylamino]-butyric acid,
(R)-4-dimethylamino-3-(8-(phenylmethanesulfonyl)-octanoylamino)-butyric acid,
(R)-3-(9-benzenesulfonyl-nonanoylamino)-4-dimethylamino-butyric acid,
and pharmaceutically acceptable salts thereof.

28. A compound of formula I according to claim 1, selected from the group consisting of
(R)-3-{7-[2-(2,3-difluoro-phenyl)-ethoxy]-heptanoylamino}-4-dimethylamino-butyric acid,
(R)-4-dimethylamino-3-[9-(methyl-phenethyl-amino)-nonanoylamino]-butyric acid,
(R)-4-dimethylamino-3-(9-phenethylamino-nonanoylamino)-butyric acid,
(R)-4-dimethylamino-3-[9-(methyl-phenyl-amino)-nonanoylamino]-butyric acid,
and pharmaceutically acceptable salts thereof.

29. A compound of formula I according to claim 1, selected from the group consisting of
(R)-4-dimethylamino-3-[8-(4-trifluoromethyl-benzyloxy)-octanoylamino]-butyric acid,
(R)-3-[8-(biphenyl-4-ylmethoxy)-octanoylamino]-4-dimethylamino-butyric acid,
(R)-4-dimethylamino-3-[9-(3-fluoro-phenoxy)-nonanoylamino]-butyric acid,
(R)-4-dimethylamino-3-[9-(4-fluoro-phenoxy)-nonanoylamino]-butyric acid,
(R)-3-[9-(3,4-difluoro-phenoxy)-nonanoylamino]-4-dimethylamino-butyric acid,
(R)-4-dimethylamino-3-[9-(2,3,4-trifluoro-phenoxy)-nonanoylamino]-butyric acid,
(R)-4-dimethylamino-3-[9-(naphthalen-1-yloxy)-nonanoylamino]-butyric acid,
(R)-4-dimethylamino-3-(10-phenyl-decanoylamino)-butyric acid,
(R)-4-dimethylamino-3-[10-(2-fluoro-phenyl)-decanoylamino]-butyric acid,
(R)-4-dimethylamino-3-(10-naphthalen-1-yl-decanoylamino)-butyric acid,
and pharmaceutically acceptable salts thereof.

30. A compound of formula I according to claim 1, selected from the group consisting of
(R)-4-dimethylamino-3-[10-(4-trifluoromethyl-phenyl)-decanoylamino]-butyric acid,
(R)-3-[10-(2,3-difluoro-phenyl)-decanoylamino]-4-dimethylamino-butyric acid,
(R)-4-dimethylamino-3-(10-thiophen-3-yl-decanoylamino)-butyric acid,
(R)-4-dimethylamino-3-(9-phenethyloxy-nonanoylamino)-butyric acid,
(R)-4-dimethylamino-3-[8-(2-phenoxy-ethoxy)-octanoylamino]-butyric acid,
and pharmaceutically acceptable salts thereof.

\* \* \* \* \*